US010591534B2

(12) United States Patent
Kotani

(10) Patent No.: US 10,591,534 B2
(45) Date of Patent: Mar. 17, 2020

(54) ELECTRONIC COMPONENT TRANSPORT APPARATUS AND ELECTRONIC COMPONENT INSPECTION APPARATUS

(71) Applicant: Seiko Epson Corporation, Tokyo (JP)

(72) Inventor: Noriaki Kotani, Hara-mura (JP)

(73) Assignee: Seiko Epson Corporation (JP)

( * ) Notice: Subject to any disclaimer, the term of this patent is extended or adjusted under 35 U.S.C. 154(b) by 138 days.

(21) Appl. No.: 15/854,164

(22) Filed: Dec. 26, 2017

(65) Prior Publication Data

US 2018/0180669 A1 Jun. 28, 2018

(30) Foreign Application Priority Data

Dec. 27, 2016 (JP) ................. 2016-252558

(51) Int. Cl.
| G01R 31/28 | (2006.01) |
| G01N 21/956 | (2006.01) |
| G01N 21/95 | (2006.01) |
| G01R 31/04 | (2006.01) |

(52) U.S. Cl.
CPC ......... *G01R 31/2891* (2013.01); *G01N 21/95* (2013.01); *G01N 21/95607* (2013.01); *G01N 21/95684* (2013.01); *G01R 31/2893* (2013.01); *G01R 31/043* (2013.01)

(58) Field of Classification Search
None
See application file for complete search history.

(56) References Cited

U.S. PATENT DOCUMENTS

| 2008/0317575 A1 | 12/2008 | Yamazaki et al. |
| 2009/0127068 A1 | 5/2009 | Ikeda et al. |
| 2009/0136118 A1 | 5/2009 | Ichikawa |
| 2012/0034052 A1 | 2/2012 | Yamazaki et al. |
| 2012/0189188 A1* | 7/2012 | Nagai ............. G06T 7/001 382/145 |
| 2018/0012351 A1* | 1/2018 | Kato ............. H05K 13/08 |
| 2019/0029153 A1* | 1/2019 | Amano ............. G01B 11/00 |

FOREIGN PATENT DOCUMENTS

| CN | 101329362 A | 12/2008 |
| JP | 2003-167022 A | 6/2003 |
| JP | 2008-290877 A | 12/2008 |
| TW | 2010-11849 A | 3/2010 |
| TW | 2011-28729 A1 | 8/2011 |
| WO | WO-2006-109358 A1 | 10/2006 |
| WO | WO-2007-017953 A1 | 2/2007 |

* cited by examiner

*Primary Examiner* — Fayyaz Alam
(74) *Attorney, Agent, or Firm* — Harness, Dickey & Pierce, P.L.C.

(57) ABSTRACT

An electronic component transport apparatus includes: an inspection region in which an inspection portion that inspects the electronic component can be disposed; a supply transport region to which the electronic component before the inspection by the inspection portion is transported; a collect transport region to which the electronic component after the inspection by the inspection portion is transported; and an imaging portion which is capable of imaging the first mounting member or the second mounting member, in which it is possible to determine at least one of the presence or absence of the electronic component and a posture of the electronic component in the first mounting member or the second mounting member based on an imaging result obtained by imaging by the imaging portion, and to notify an operator of a determination result.

14 Claims, 14 Drawing Sheets

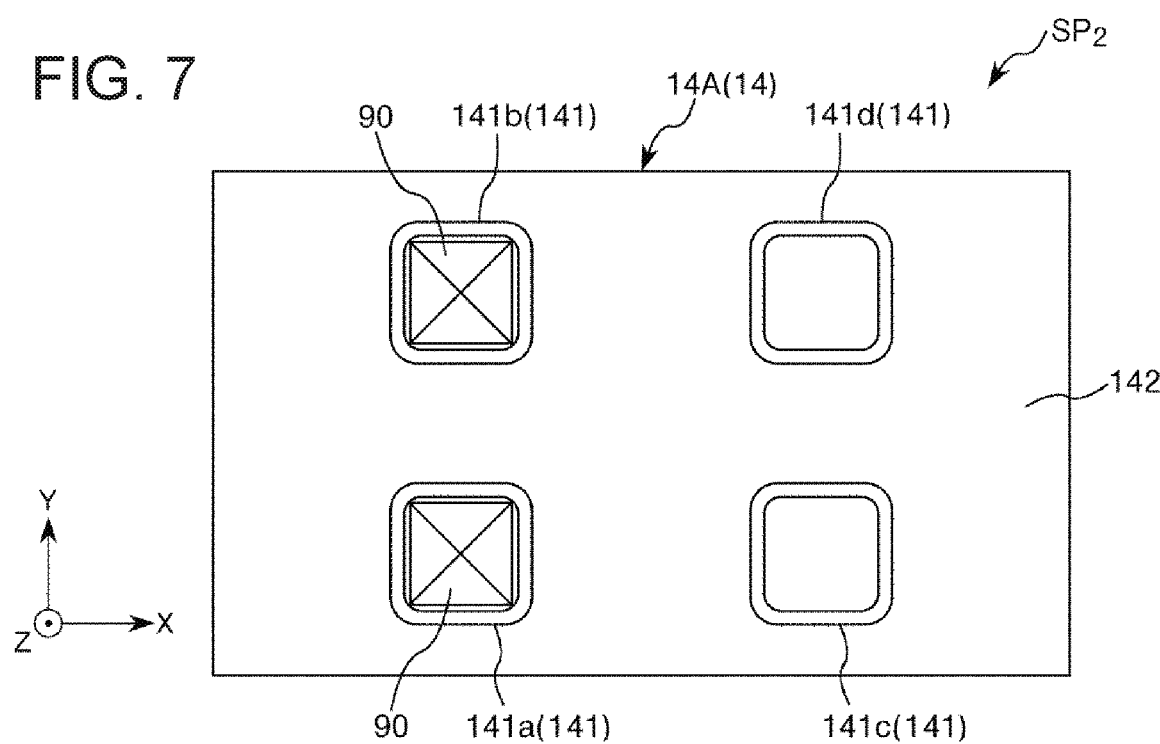
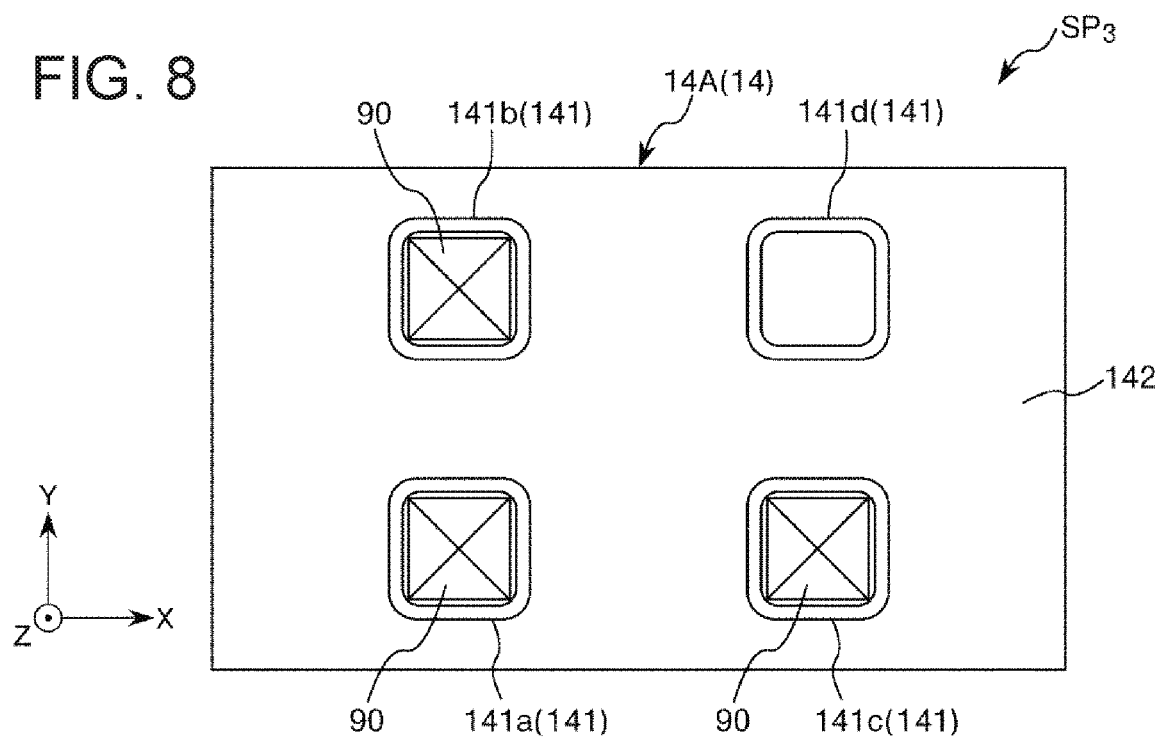

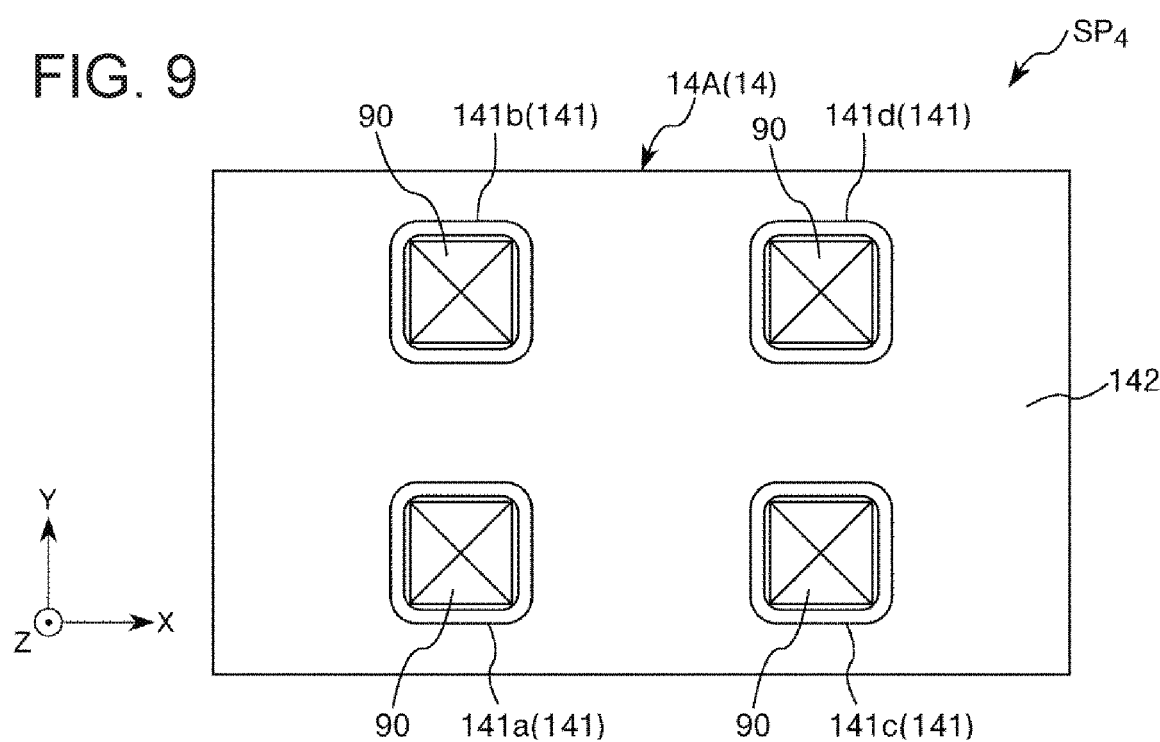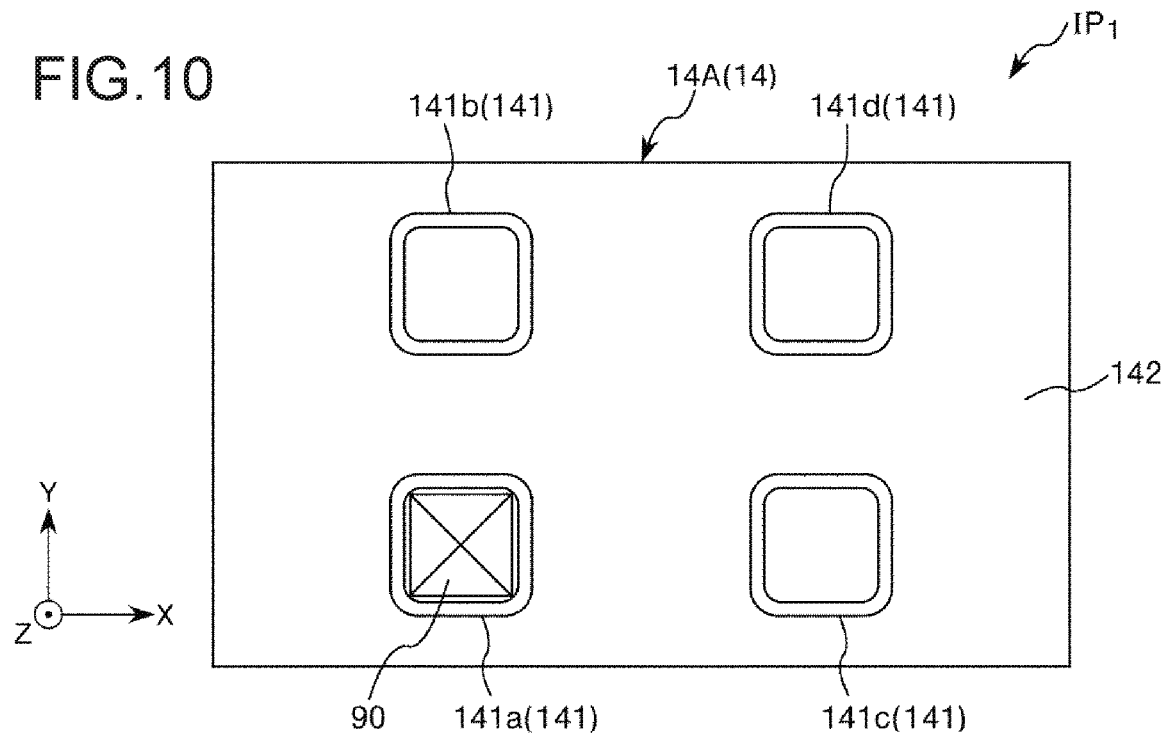

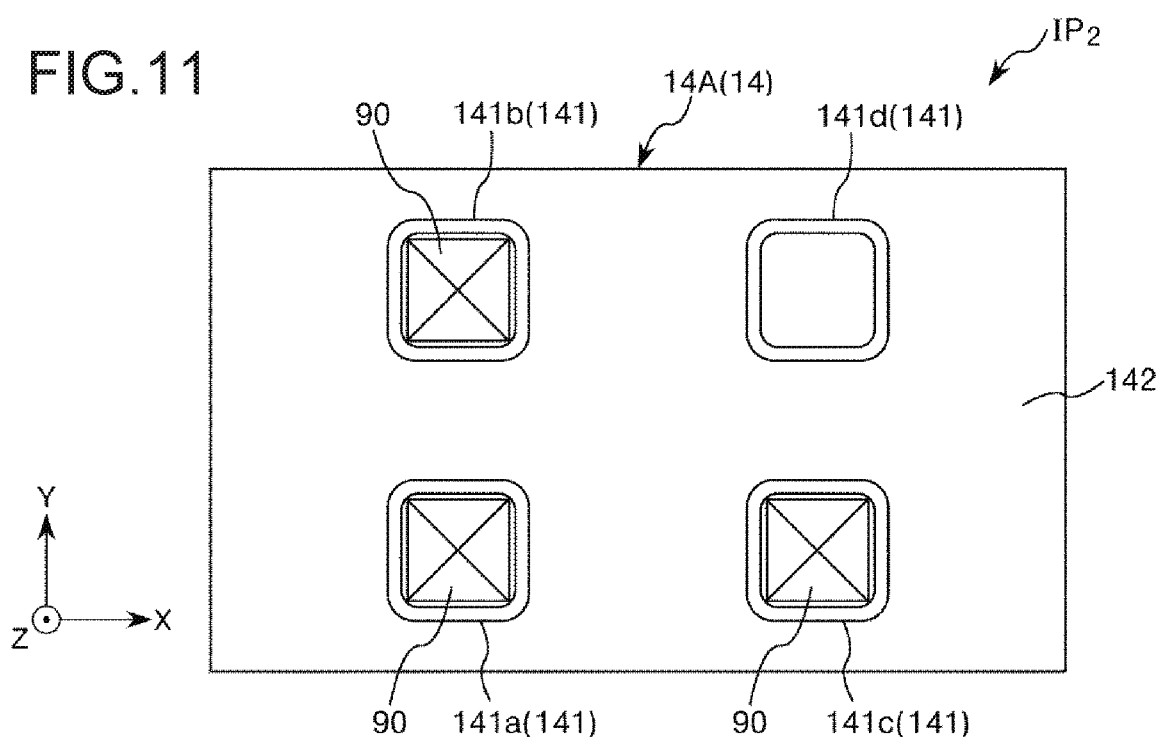
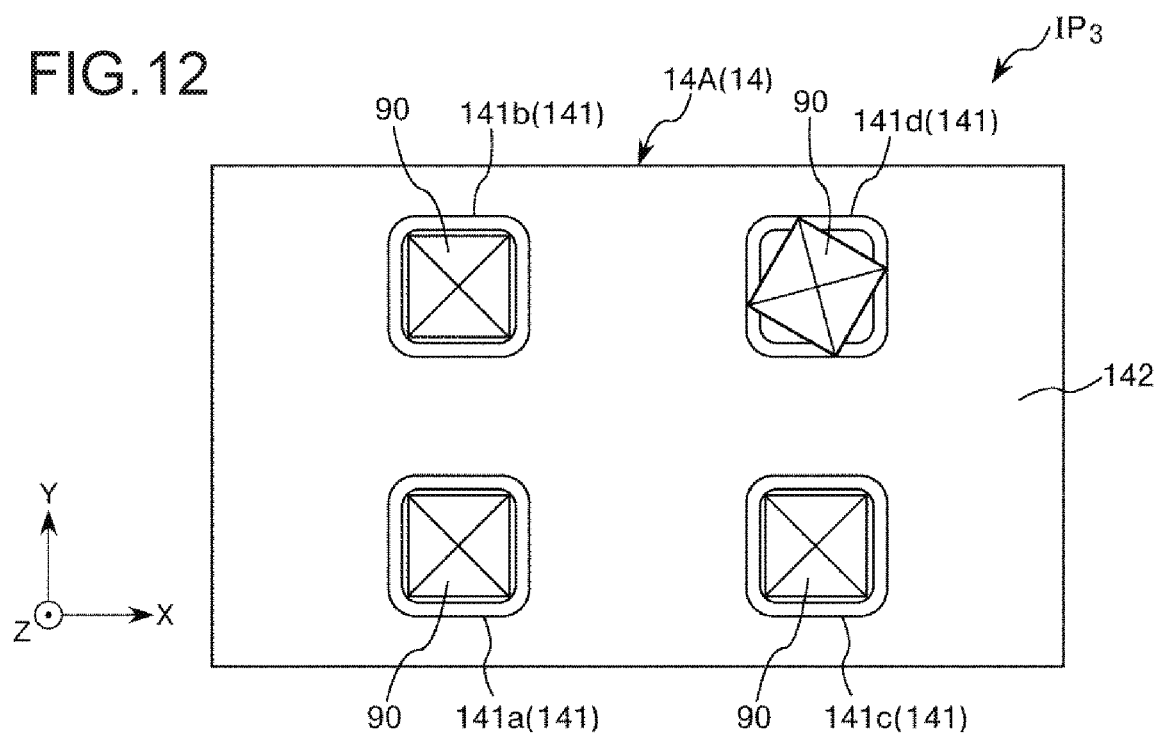

ELECTRONIC COMPONENT TRANSPORT APPARATUS AND ELECTRONIC COMPONENT INSPECTION APPARATUS

BACKGROUND

1. Technical Field

The present invention relates to an electronic component transport apparatus and an electronic component inspection apparatus.

2. Related Art

From the related art, an electronic component inspection apparatus which inspects electric characteristics of an electronic component, such as an IC device, is known, and an electronic component transport apparatus for transporting the IC device is incorporated in the electronic component inspection apparatus (for example, refer to International Publication No. 2006/109358).

In the electronic component transport apparatus described in International Publication No. 2006/109358, in a state where the transport of the electronic component is not performed, the image of a socket (inspection portion) to which inspection of the electronic component is performed is captured, the image is stored in advance as reference image data. In addition, a configuration in which the image of the socket is captured during the transport of the electronic component and the image is compared with the reference image data, is employed. Accordingly, it is possible to detect mounting abnormality or the like in the socket.

However, in an electronic component inspection apparatus described in International Publication No. 2006/109358, similar to a socket, a heat plate, a buffer portion for a loader, a buffer portion for an unloader and the like which function as mounting members on which an IC device is mounted, are provided, but it is not possible to detect (determine) mounting abnormality or the like by the mounting members. In addition, after the detection, for example, it is not possible to notify an operator of a warning, either.

SUMMARY

An advantage of some aspects of the invention is to solve at least a part of the problems described above, and the invention can be implemented in the following configurations.

An electronic component transport apparatus according to an aspect of the invention includes: a transport portion which is capable of transporting an electronic component; an inspection region in which an inspection portion that inspects the electronic component can be disposed; a supply transport region in which a first mounting member including a plurality of first mounting portions on which the electronic component is mounted can be disposed, and to which the electronic component before the inspection by the inspection portion is transported; a collect transport region in which a second mounting member including a plurality of second mounting portions on which the electronic component is mounted can be disposed, and to which the electronic component after the inspection by the inspection portion is transported; and an imaging portion which is capable of imaging at least one of the first mounting member or the second mounting member, in which it is possible to determine at least one of the presence or absence of the electronic component and a posture of the electronic component in the first mounting member or the second mounting member based on an imaging result obtained by imaging by the imaging portion, and to notify an operator of a determination result.

With this configuration, for example, the operator who has confirmed the notification can visually recognize a state of the electronic component in the first mounting member or the second mounting member, and to take a countermeasure (for example, removal of the electronic component or correction of the posture of the electronic component) which corresponds to the state. Accordingly, it is possible to prevent generation of a defect that the electronic component is damaged or the like, and thus, a transport operation of the electronic component is stably and rapidly performed.

In the electronic component transport apparatus according to the aspect of the invention, it is preferable that the imaging portion is disposed in the supply transport region.

With this configuration, it is possible to image the first mounting member in the supply transport region, and thus, it is possible to determine at least one of the presence or absence of the electronic component and the posture of the electronic component in the first mounting member, and to notify the operator of the determination result.

In the electronic component transport apparatus according to the aspect of the invention, it is preferable that the imaging portion is disposed in the collect transport region.

With this configuration, it is possible to image the second mounting member of the collect transport region, and thus, it is possible to determine at least one of the presence or absence of the electronic component and the posture of the electronic component in the second mounting member, and to notify the operator of the determination result.

In the electronic component transport apparatus according to the aspect of the invention, it is preferable that the imaging portion is disposed in the supply transport region and in the collect transport region.

With this configuration, it is possible to image the first mounting member in the supply transport region, and thus, it is possible to determine at least one of the presence or absence of the electronic component and the posture of the electronic component in the first mounting member, and to notify the operator of the determination result, and at the same time, it is possible to image the second mounting member of the collect transport region, and thus, it is possible to determine at least one of the presence or absence of the electronic component and the posture of the electronic component by the second mounting member, and to notify the operator of the determination result.

In the electronic component transport apparatus, it is preferable that it is possible to determine at least one of the presence or absence of the electronic component and the posture of the electronic component by comparing imaging data obtained by imaging by the imaging portion and reference data set in advance to each other, and to notify an operator of the determination result.

With this configuration, it is possible to rapidly and accurately determine at least one of the presence or absence of the electronic component and the posture of the electronic component.

In the electronic component transport apparatus according to the aspect of the invention, it is preferable that an inclination of the electronic component and a positional shift of the electronic component are included in the posture.

The inclination and the positional shift are a posture that can be relatively easily generated in an inappropriate posture, and a case where the inclination and the positional shift are included in the posture is preferable for the notification of the determination result.

In the electronic component transport apparatus according to the aspect of the invention, it is preferable that the imaging portion is disposed above the first mounting member or the second mounting member in one of the regions.

With this configuration, it is possible to ensure an imaging region as wide as possible, and to image the entire first mounting member or the second mounting member which are imaging targets.

In the electronic component transport apparatus according to the aspect of the invention, it is preferable that the transport portion includes a transport head which is disposed in one of the regions, and grips and transports the electronic component, and the transport head is movable downward from the imaging portion.

With this configuration, it is possible to prevent interference with the imaging portion even when the transport head has moved.

In the electronic component transport apparatus according to the aspect of the invention, it is preferable that the first mounting member is at least one of a shuttle that is capable of reciprocating between the supply transport region and the inspection region, a temperature adjustment portion which is capable of adjusting the temperature of the electronic component, and a tray on which the electronic component before being transported in the supply transport region is mounted.

With this configuration, for example, the operator who has confirmed the notification can visually recognize the state of the electronic component of the shuttle, the temperature adjustment portion, or the tray, which is the first mounting member, and can take a countermeasure (for example, removal of the electronic component or correction of the posture of the electronic component) which corresponds to the state. Accordingly, it is possible to prevent generation of a defect that the electronic component is damaged or the like, and thus, the transport operation of the electronic component is stably and rapidly performed.

In the electronic component transport apparatus according to the aspect of the invention, it is preferable that the second mounting member is at least one of a shuttle that is capable of reciprocating between the inspection region and the collect transport region, and a tray on which the electronic component after being transported in the collect transport region is mounted.

With this configuration, for example, the operator who has confirmed the notification can visually recognize the state of the electronic component of the shuttle or the tray, which is the second mounting member, and can take a countermeasure (for example, removal of the electronic component or correction of the posture of the electronic component) which corresponds to the state. Accordingly, it is possible to prevent generation of a defect that the electronic component is damaged or the like, and thus, the transport operation of the electronic component is stably and rapidly performed.

In the electronic component transport apparatus according to the aspect of the invention, it is preferable that the imaging portion is capable of dividing and imaging the first mounting member or the second mounting member in one of the regions.

With this configuration, regardless of the size of the first mounting member or the second mounting member in one of the regions, it is possible to obtain an image of the entire mounting member. Accordingly, it is possible to determine the state (the presence or absence of the electronic component or the posture of the electronic component) of the mounting member.

In the electronic component transport apparatus according to the aspect of the invention, it is preferable that different notifications are performed in a case where the presence or absence of the electronic component is determined and in a case where the posture of the electronic component is determined.

With this configuration, the operator can grasp in which state the first mounting member or the second mounting member in one of the regions is, and in accordance with the state, it is possible to take an appropriate countermeasure.

In the electronic component transport apparatus according to the aspect of the invention, it is preferable that at least one mounting portion of the first mounting portion and the second mounting portion is configured of a recess portion, and plural types of reflectors having different degrees of reflection of light are replaceable and installable in a bottom portion of the recess portion before the electronic component is mounted.

With this configuration, it is possible to change the contrast of the electronic component and the reflector in the image captured by the imaging portion. In addition, by exchanging the reflector in accordance with the brightness in one of the regions, it is possible to determine the posture of the electronic component.

An electronic component inspection apparatus according to an aspect of the invention includes: a transport portion which is capable of transporting an electronic component; an inspection portion which inspects the electronic component; an inspection region in which the inspection portion that inspects the electronic component can be disposed; a supply transport region in which a first mounting member including a plurality of first mounting portions on which the electronic component is mounted can be disposed, and to which the electronic component before the inspection by the inspection portion is transported; a collect transport region in which a second mounting member including a plurality of second mounting portions on which the electronic component is mounted can be disposed, and to which the electronic component after the inspection by the inspection portion is transported; and an imaging portion which is capable of imaging at least one of the first mounting member or the second mounting member, in which it is possible to determine at least one of the presence or absence of the electronic component and a posture of the electronic component in the first mounting member or the second mounting member based on an imaging result obtained by imaging by the imaging portion, and to notify an operator of a determination result.

With this configuration, for example, the operator who has confirmed the notification can visually recognize the state of the electronic component in the first mounting member or the second mounting member, and can take a countermeasure (for example, removal of the electronic component or correction of the posture of the electronic component) which corresponds to the state. Accordingly, it is possible to prevent generation of a defect that the electronic component is damaged or the like, and thus, the transport operation of the electronic component is stably and rapidly performed.

In addition, it is possible to transport the electronic component to the inspection portion, and thus, to perform the inspection with respect to the electronic component by the inspection portion. In addition, it is possible to transport the electronic component after the inspection from the inspection portion.

BRIEF DESCRIPTION OF THE DRAWINGS

The invention will be described with reference to the accompanying drawings, wherein like numbers reference like elements.

FIG. 7 is an example of the reference image stored in advance in the electronic component inspection apparatus illustrated in FIG. 1.

FIG. 8 is an example of the reference image stored in advance in the electronic component inspection apparatus illustrated in FIG. 1.

FIG. 9 is an example of the reference image stored in advance in the electronic component inspection apparatus illustrated in FIG. 1.

FIG. 10 is an example of the image (captured image) of a supply shuttle captured by the imaging portion illustrated in FIG. 3.

FIG. 11 is an example of the image (captured image) of the supply shuttle captured by the imaging portion illustrated in FIG. 3.

FIG. 12 is an example of the image (captured image) of a supply shuttle captured by the imaging portion illustrated in FIG. 3.

DESCRIPTION OF EXEMPLARY EMBODIMENTS

Hereinafter, an electronic component transport apparatus and an electronic component inspection apparatus according to the invention will be described in detail based on appropriate embodiments illustrated in the attached drawings.

First Embodiment

Figure 1:
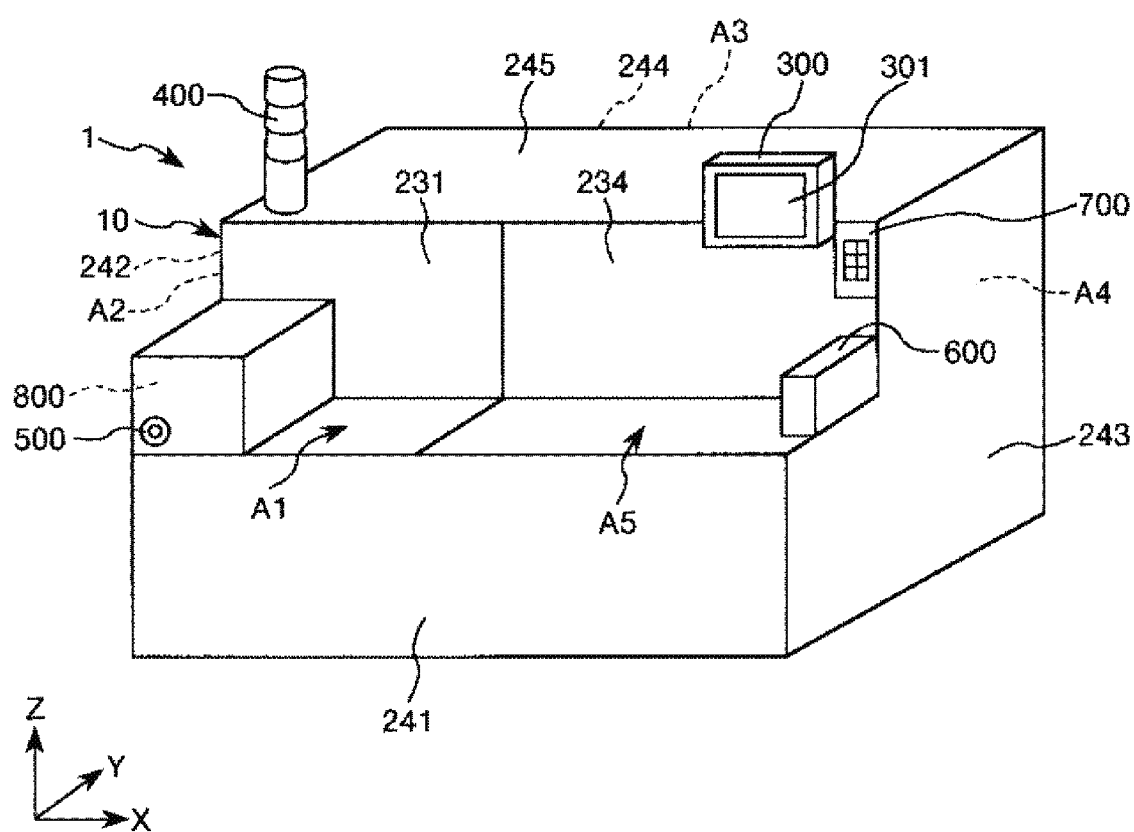
FIG. 1 is a schematic perspective view when a first embodiment of an electronic component inspection apparatus according to the invention is viewed from a front side.

Hereinafter, a first embodiment of the electronic component transport apparatus and the electronic component inspection apparatus according to the invention will be described with reference to FIGS. 1 to 18. In addition, hereinafter, for the convenience of the description, as illustrated in FIG. 1, three axes which are orthogonal to each other are an X-axis, a Y-axis, and a Z-axis. In addition, an XY plane including the X-axis and the Y-axis is horizontal, and the Z-axis is perpendicular. In addition, a direction parallel to the X-axis is also referred to as "X direction (first direction)", a direction parallel to the Y-axis is also referred to as "Y direction (second direction)", and a direction parallel to the Z-axis is also referred to as "Z direction (third direction)". In addition, a direction in which arrows of each direction are oriented is "positive", and a direction opposite thereto is "negative". In addition, "horizontal" referred in the specification is not limited to a complete horizontal state, and also includes a state of being slightly (for example, a degree which is less than 5°) inclined with respect to the horizontal state as long as transport of an electronic component is not interrupted. In addition, an upper side, that is, a positive side in the Z-axis direction in FIGS. 1 and 4 (similar in FIGS. 19 and 20) is referred to as "up" or "upper part", and a lower side, that is, a negative side in the Z-axis direction is referred to as "down" or "lower part".

An electronic component transport apparatus 10 according to the invention has an external appearance illustrated in FIG. 1. The electronic component transport apparatus 10 according to the invention is a handler, and as illustrated in FIG. 3, includes: a transport portion 25 which can transport the electronic component; an inspection region A3 in which an inspection portion 16 that inspects the electronic component can be disposed; a device supply region A2 (supply transport region) in which a first mounting member (device supply portion 14) including a plurality of first mounting portions on which the electronic component is mounted can be disposed, and to which the electronic component before the inspection by the inspection portion 16 is transported; a device collect region A4 (collect transport region) in which a second mounting member including a plurality of second mounting portions on which the electronic component is mounted can be disposed, and to which the electronic component after the inspection by the inspection portion 16 is transported; and an imaging portion 26 which can image the first mounting member (device supply portion 14) or the second mounting member, can determine at least one of the presence or absence of the electronic component and the posture of the electronic component in the first mounting member (device supply portion 14) or the second mounting member based on an imaging result obtained by imaging by the imaging portion 26, and can notify an operator of the determination result.

Accordingly, as will be described later, for example, the operator who has confirmed the notification can visually recognize a state of the electronic component in the first mounting member (device supply portion 14) or the second mounting member, and to take a countermeasure (for example, removal of the electronic component or correction of the posture of the electronic component) which corresponds to the state. Accordingly, it is possible to prevent generation of a defect that the electronic component is damaged or the like, and thus, a transport operation of the electronic component is stably and rapidly performed.

Figure 2:
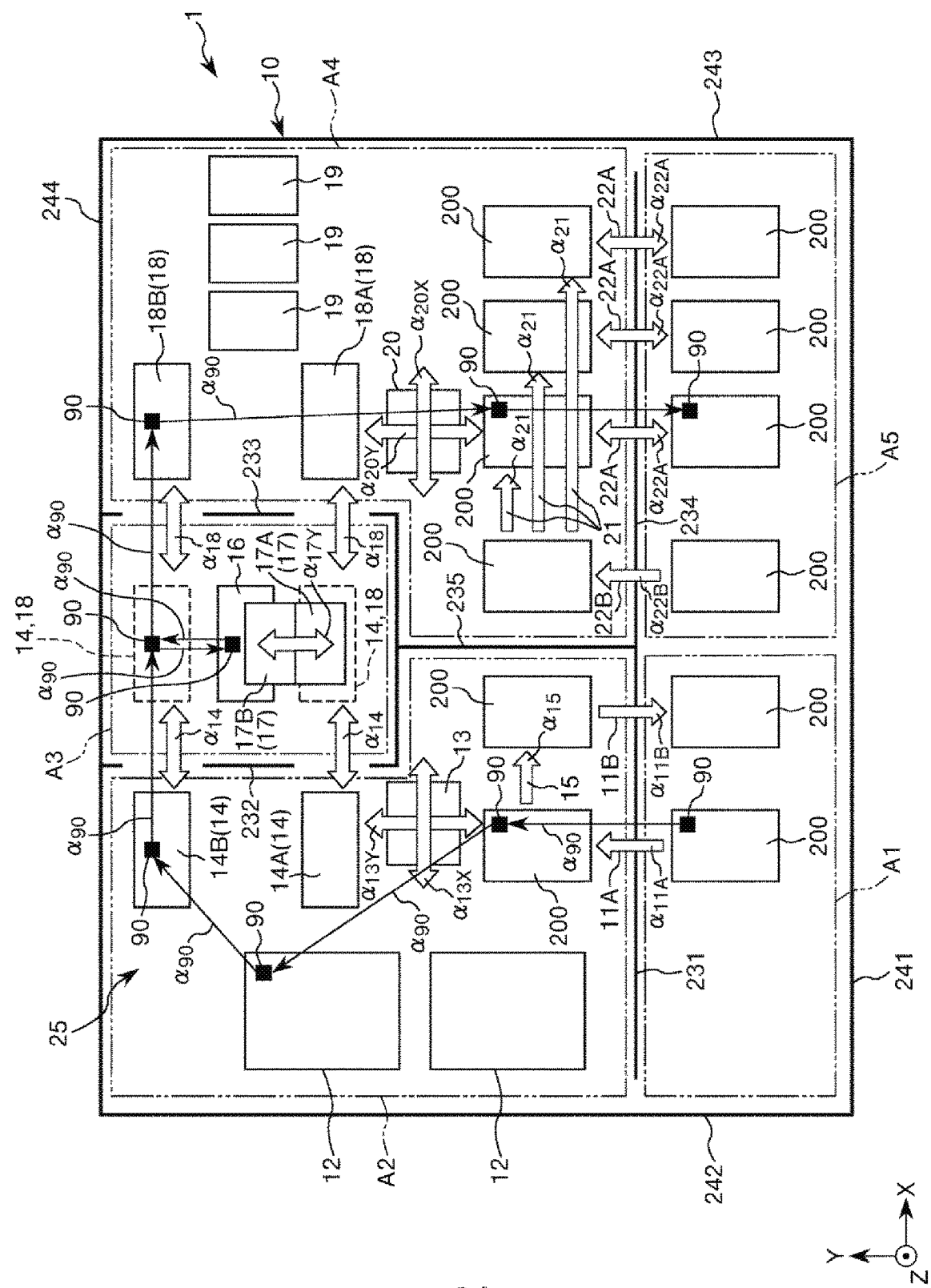
FIG. 2 is a schematic plan view illustrating an operation state of the electronic component inspection apparatus illustrated in FIG. 1.
Figure 3:
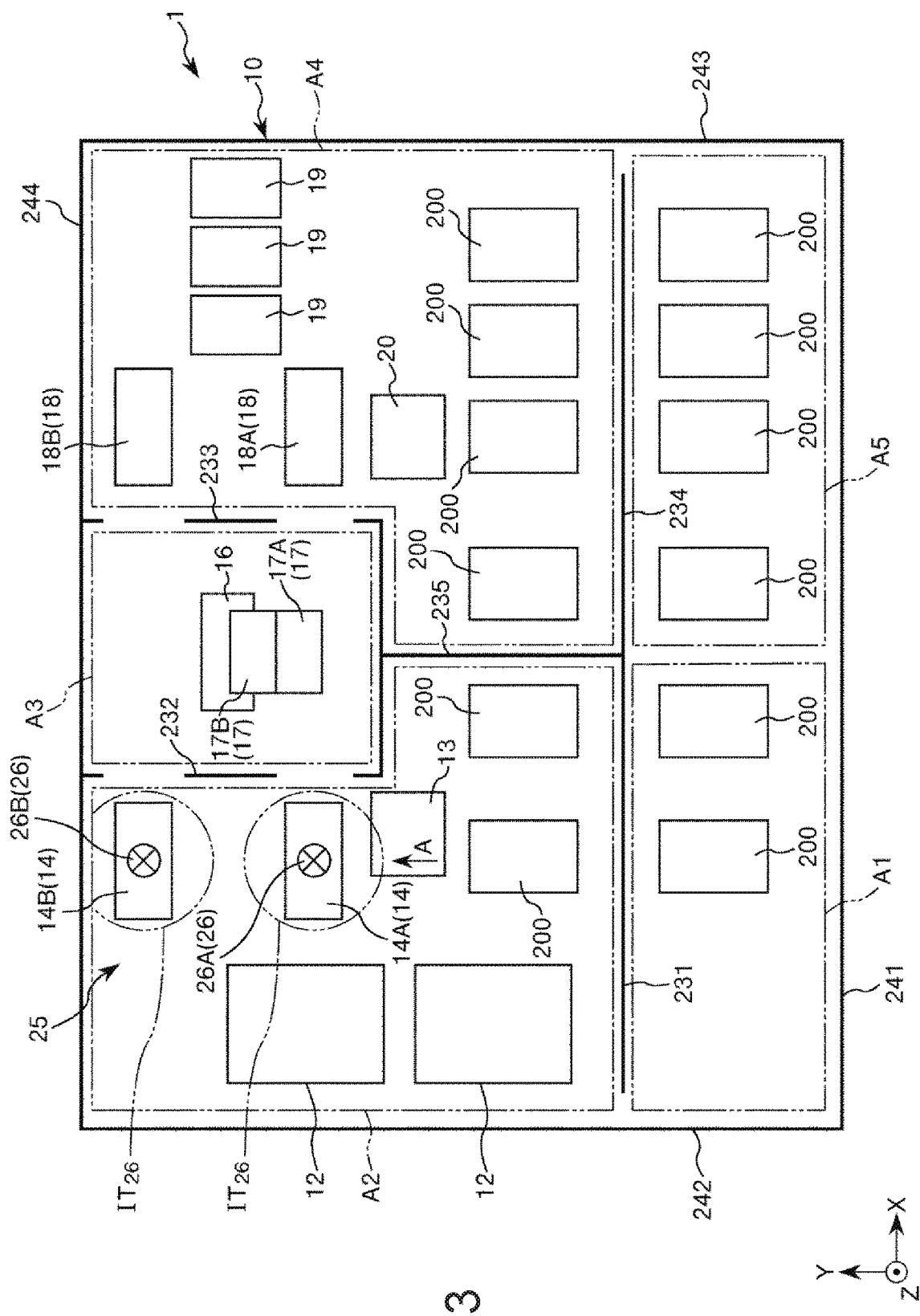
FIG. 3 is a plan view illustrating a disposition state of an imaging portion in the electronic component inspection apparatus illustrated in FIG. 1.

In addition, as illustrated in FIGS. 2 and 3, an electronic component inspection apparatus 1 according to the invention includes the electronic component transport apparatus 10, and further includes the inspection portion 16 that inspects the electronic component. In other words, the electronic component inspection apparatus 1 according to the invention includes: the transport portion 25 which can transport the electronic component; the inspection portion 16 which inspects the electronic component; the inspection region A3 in which the inspection portion 16 can be disposed; the device supply region A2 (supply transport region) in which the first mounting member (device supply portion 14) including the plurality of first mounting portions on which the electronic component is mounted can be disposed, and to which the electronic component before the inspection by the inspection portion 16 is transported; the device collect region A4 (collect transport region) in which the second mounting member including the plurality of second mounting portions on which the electronic component is mounted can be disposed, and to which the electronic component after the inspection by the inspection portion 16 is transported; and the imaging portion 26 which can image the first mounting member or the second mounting member, can determine at least one of the presence or absence of the electronic component and the posture of the electronic component in the first mounting member (device supply portion 14) or the second mounting member based on the imaging result obtained by imaging by the imaging portion 26, and can notify the operator of the determination result.

Accordingly, the electronic component inspection apparatus 1 having an advantage of the above-described electronic component transport apparatus 10 is obtained. In addition, it is possible to transport the electronic component to the inspection portion 16, and thus, to perform the inspection with respect to the electronic component by the inspection portion 16. In addition, it is possible to transport the electronic component after the inspection from the inspection portion 16.

Hereinafter, configurations of each portion will be described in detail.

As illustrated in FIGS. 1 and 2, the electronic component inspection apparatus 1 having the electronic component transport apparatus 10 embedded therein is an apparatus which transports the electronic component, such as an IC device, which is a ball grid array (BGA) package, and inspects and tests (hereinafter, simply referred to as "inspection") electric characteristics of the electronic component in the transport process. In addition, hereinafter, for the convenience of the description, a case where the IC device which functions as the electronic component is used will be described as a representative example, and this will be referred to as "IC device 90". The IC device 90 has a shape of a flat plate in the embodiment.

In addition to the description above, examples of the IC device include "large scale integration (LSI)", "complementary MOS (CMOS)", "charge coupled device (CCD)", "module IC" in which the plurality of IC devices are made as a module package, "quartz device", "pressure sensor", "inertial sensor (acceleration sensor)", "gyro sensor", and "fingerprint sensor".

The electronic component inspection apparatus 1 (electronic component transport apparatus 10) includes a tray supply region A1, the device supply region A2, the inspection region A3, the device collect region A4, and a tray remove region A5, and the regions are divided by each of wall portions as will be described later. In addition, the IC device 90 is inspected in the inspection region A3 in the middle of the path via each of the regions from the tray supply region A1 to the tray remove region A5 in order in an arrow $\alpha_{90}$ direction. In this manner, the electronic component inspection apparatus 1 includes the electronic component transport apparatus 10 including the transport portion 25 which transports the IC device 90 via each of the regions, the inspection portion 16 which performs the inspection in the inspection region A3, and a control portion 800. In addition to this, the electronic component inspection apparatus 1 includes a monitor 300, a signal lamp 400, and an operation panel 700.

In addition, in the electronic component inspection apparatus 1, it means that a part at which the tray supply region A1 and the tray remove region A5 are disposed, that is, a lower side in FIGS. 2 and 3 is a front side, and a part in which the inspection region A3 is disposed, that is, an upper side in FIGS. 2 and 3 is a rear side.

In addition, the electronic component inspection apparatus 1 is used while a so-called "change kit" which is exchanged for each type of the IC device 90 is loaded in advance. In the change kit, there is a mounting member on which the IC device 90 is mounted, and as the mounting member, there are the first mounting member disposed in the device supply region A2 and the second mounting member disposed in the device collect region A4. As the first mounting member, for example, there are a temperature adjustment portion 12 which will be described later and the device supply portion 14. As the second mounting member, for example, there is a device collect portion 18 which will be described later. In addition, as the mounting member on which the IC device 90 is mounted, in addition to the change kit described above, there are also a tray 200, a tray for collection 19, and the inspection portion 16 which will be prepared by a user. The tray 200 disposed in the device supply region A2 can be called the first mounting member, and the tray 200 and the tray for collection 19 which are disposed in the device collect region A4 can be called the second mounting member.

The tray supply region A1 is a material supply portion by which the tray 200 on which the plurality of IC devices 90 in a state of not being inspected are arranged is supplied. It can be said that the tray supply region A1 is a loading region in which the plurality of trays 200 can be stacked and loaded. In addition, in the embodiment, in each of the trays 200, a plurality of recess portions (pockets) are disposed in a shape of a matrix. Each of the recess portions is a mounting portion which can accommodate and mount the IC devices 90 one by one.

The device supply region A2 is a region through which the plurality of IC devices 90 on the tray 200 transported from the tray supply region A1 are respectively transported and supplied to the inspection region A3. In addition, tray transport mechanisms 11A and 11B which transport the trays 200 in the horizontal direction one by one are provided to go across the tray supply region A1 and the device supply region A2. The tray transport mechanism 11A is a part of the transport portion 25, and the tray 200 can be moved to the positive side in the Y direction for each of the IC devices 90 mounted on the tray 200, that is, in an arrow $\alpha_{11A}$ direction in FIG. 2. Accordingly, it is possible to stably send the IC device 90 into the device supply region A2. In addition, the tray transport mechanism 11B is a moving portion which can move the empty tray 200 to the negative side in the Y direction, that is, in an arrow $\alpha_{11B}$ direction in FIG. 2. Accordingly, it is possible to move the empty tray 200 from the device supply region A2 to the tray supply region A1.

In the device supply region A2, the temperature adjustment portion (soak plate (vapor chamber in Chinese (an example))) 12, a device transport head 13, and a tray transport mechanism 15, are provided. In addition, the device supply portion 14 which moves to go across the device supply region A2 and the inspection region A3 is also provided.

The temperature adjustment portion 12 is a mounting member on which the plurality of IC devices 90 are mounted, and is called "soak plate" which can collectively heat or cool the mounted IC device 90. By using the soak plate, it is possible to heat or cool the IC device 90 before the inspection by the inspection portion 16 in advance, and to adjust the temperature to the temperature appropriate for the inspection (high temperature inspection or low temperature inspection). In the configuration illustrated in FIG. 2 (also similar in FIG. 3), two temperature adjustment portions 12 are disposed and fixed in the Y direction. In addition, the IC device 90 on the tray 200 transported in from the tray supply region A1 by the tray transport mechanism 11A is transported to any of the temperature adjustment portions 12. In addition, as the temperature adjustment portion 12 which functions as the mounting member is fixed, it is possible to stably adjust the temperature with respect to the IC device 90 on the temperature adjustment portion 12. In addition, the temperature adjustment portion 12 is grounded.

The device transport head 13 is a gripping portion which grips the IC device 90, is supported to be movable in the X direction and in the Y direction in the device supply region A2, and is further supported to be movable in the Z direction. The device transport head 13 is also a part of the transport portion 25, and can transport the IC device 90 between the tray 200 transported in from the tray supply region A1 and the temperature adjustment portion 12 and transport the IC device 90 between the temperature adjustment portion 12 and the device supply portion 14 which will be described later. In addition, in FIG. 2, the movement of the device transport head 13 in the X direction is illustrated as an arrow $\alpha_{13X}$, and the movement of the device transport head 13 in the Y direction is illustrated as an arrow $\alpha_{13Y}$.

The device supply portion 14 is a mounting member on which the IC device 90 of which the temperature is adjusted by the temperature adjustment portion 12 is mounted, and is also called "shuttle plate for supply" or simply "supply shuttle" which can transport the IC device 90 to the vicinity of the inspection portion 16. The device supply portion 14 can also be a part of the transport portion 25.

In addition, the device supply portion 14 which functions as the mounting member is supported to be capable of reciprocating between the device supply region A2 and the inspection region A3 along the X direction, that is, along an arrow $\alpha_{14}$ direction. Accordingly, the device supply portion 14 can stably transport the IC device 90 from the device supply region A2 to the vicinity of the inspection portion 16 of the inspection region A3, and can return to the device supply region A2 again after the IC device 90 is removed by a device transport head 17 in the inspection region A3.

In the configuration illustrated in FIG. 2, two device supply portions 14 are disposed in the Y direction, the device supply portion 14 on the negative side in the Y direction is called "device supply portion 14A", and the device supply portion 14 on the positive side in the Y direction is called "device supply portion 14B". In addition, the IC device 90 on the temperature adjustment portion 12 is transported to the device supply portion 14A or the device supply portion 14B in the device supply region A2. In addition, similar to the temperature adjustment portion 12, the device supply portion 14 is configured to be capable of heating or cooling the IC device 90 mounted on the device supply portion 14. Accordingly, with respect to the IC device 90 of which the temperature is adjusted by the temperature adjustment portion 12, it is possible to maintain the temperature adjustment state, and to transport the IC device 90 to the vicinity of the inspection portion 16 of the inspection region A3. In addition, similar to the temperature adjustment portion 12, the device supply portion 14 is also grounded.

The tray transport mechanism 15 is a mechanism which transports the empty tray 200 in a state where all of the IC devices 90 are removed to the positive side in the X direction in the device supply region A2, that is, in an arrow $\alpha_{15}$ direction. In addition, after the transport, the empty tray 200 returns to the tray supply region A1 from the device supply region A2 by the tray transport mechanism 11B.

The inspection region A3 is a region in which the IC device 90 is inspected. In the inspection region A3, the inspection portion 16 which performs the inspection with respect to the IC device 90, and the device transport head 17 are provided.

The device transport head 17 is a part of the transport portion 25, the IC device 90 maintained in the temperature adjustment state can be gripped, and the IC device 90 can be transported in the inspection region A3. The device transport head 17 is a part of a mechanism which is supported to be capable of reciprocating in the Y direction and in the Z direction in the inspection region A3, and is called "index arm". Accordingly, the device transport head 17 can transport and mount the IC device 90 on the device supply portion 14 transported in from the device supply region A2 onto the inspection portion 16. In addition, in FIG. 2, the reciprocating movement of the device transport head 17 in the Y direction is illustrated by an arrow $\alpha_{17Y}$. In addition, the device transport head 17 is supported to be capable of reciprocating in the Y direction, but not being limited thereto, the device transport head 17 may also be supported to be capable of reciprocating in the X direction. In addition, in the configuration illustrated in FIG. 2, two device transport heads 17 are disposed in the Y direction, the device transport head 17 on the negative side in the Y direction is called "device transport head 17A", and the device transport head 17 on the positive side in the Y direction is called "device transport head 17B". The device transport head 17A can transport the IC device 90 from the device supply portion 14A to the inspection portion 16 in the inspection region A3, and the device transport head 17B can transport the IC device 90 from the device supply portion 14B to the inspection portion 16 in the inspection region A3.

In addition, similar to the temperature adjustment portion 12, the device transport head 17 is configured to be capable of heating and cooling the gripped IC device 90. Accordingly, the temperature adjustment state in the IC device 90 can be continuously maintained from the device supply portion 14 to the inspection portion 16.

The inspection portion 16 is a mounting member on which the IC device 90 which is the electronic component is mounted and inspects the electric characteristics of the IC device 90. In the inspection portion 16, a plurality of probe pins which are electrically connected to a terminal of the IC device 90 are provided. In addition, as the terminal of the IC device 90 and the probe pin are electrically connected to each other, that is, come into contact with each other, the IC device 90 can be inspected. The inspection of the IC device 90 is performed based on a program which is stored in an inspection control portion including a tester connected to the inspection portion 16. In addition, even in the inspection portion 16, similar to the temperature adjustment portion 12, the IC device 90 can be heated or cooled, and the temperature of the IC device 90 can be adjusted to the temperature appropriate for the inspection.

The device collect region A4 is a region in which the plurality of IC devices 90 which are inspected in the inspection region A3 and of which the inspection is finished are collected. In the device collect region A4, the tray for collection 19, a device transport head 20, and a tray transport mechanism 21 are provided. In addition, the device collect portion 18 which moves to go through the inspection region A3 and the device collect region A4 is also provided. In addition, in the device collect region A4, the empty tray 200 is also prepared.

The device collect portion 18 is a mounting member on which the IC device 90 of which the inspection is finished by the inspection portion 16 is mounted, and which can transport the IC device 90 to the device collect region A4, and is called "shuttle plate for collection" or simply "collect shuttle". The device collect portion 18 can also be a part of the transport portion 25.

In addition, the device collect portion 18 is supported to be capable of reciprocating in the X direction between the inspection region A3 and the device collect region A4, that is, along an arrow $\alpha_{18}$ direction. In addition, in the configuration illustrated in FIG. 2, similar to the device supply portion 14, two device collect portions 18 are disposed in the Y direction, the device collect portion 18 on the negative side in the Y direction is called "device collect portion 18A", and the device collect portion 18 on the positive side in the Y direction is called "device collect portion 18B". In addition, the IC device 90 on the inspection portion 16 is transported and mounted to the device collect portion 18A or the device collect portion 18B. In addition, the transport of the IC device 90 from the inspection portion 16 to the device collect portion 18A is performed by the device transport head 17A, and the transport of the IC device 90 from the inspection portion 16 to the device collect portion 18B is performed by the device transport head 17B. In addition, similar to the temperature adjustment portion 12 or the device supply portion 14, the device collect portion 18 is also grounded.

The tray for collection 19 is a mounting member on which the IC device 90 inspected by the inspection portion 16 is mounted, and is fixed not to move in the device collect region A4. Accordingly, even in the device collect region A4 in which a relatively large number of various types of movable portions are disposed, such as the device transport head 20, are disposed the IC device 90 which is already inspected is stably mounted on the tray for collection 19. In addition, in the configuration illustrated in FIG. 2, three trays for collection 19 are disposed along the X direction.

In addition, three empty trays 200 are disposed along the X direction. The empty tray 200 is also a mounting member on which the IC device 90 inspected by the inspection portion 16 is mounted. In addition, the IC device 90 on the device collect portion 18 that has moved to the device collect region A4 is transported and mounted to any of the tray for collection 19 and the empty tray 200. Accordingly, the IC device 90 is classified for each of the inspection result, and is collected.

The device transport head 20 is supported to be movable in the X direction and in the Y direction in the device collect region A4, and further has a part that can also move in the Z direction. The device transport head 20 is a part of the transport portion 25, and can transport the IC device 90 to the tray for collection 19 or the empty tray 200 from the device collect portion 18. In addition, in FIG. 2, the movement of the device transport head 20 in the X direction is illustrated by an arrow $\alpha_{20X}$, and the movement of the device transport head 20 in the Y direction is illustrated by an arrow $\alpha_{20Y}$.

The tray transport mechanism 21 is a mechanism which transports the empty tray 200 transported in from the tray remove region A5 in the X direction in the device collect region A4, that is, in an arrow $\alpha_{21}$ direction. In addition, after the transport, the empty tray 200 can be disposed at a position at which the IC device 90 is collected, that is, can be any of the three empty trays 200.

The tray remove region A5 is a material remove portion which collects and removes the tray 200 on which the plurality of IC devices 90 in an inspected state are arranged. In the tray remove region A5, it is possible to stack multiple trays 200.

In addition, a tray transport mechanism 22A and a tray transport mechanism 22B which transport the trays 200 in the Y direction one by one are provided to go across the device collect region A4 and the tray remove region A5. The tray transport mechanism 22A is a moving portion which is a part of the transport portion 25 and can allow the tray 200 to reciprocate in the Y direction, that is, in an arrow $\alpha_{22A}$ direction. Accordingly, it is possible to transport the IC device 90 that is already inspected from the device collect region A4 to the tray remove region A5. In addition, the tray transport mechanism 22B can move the empty tray 200 for collecting the IC device 90 to the positive side in the Y direction, that is, in an arrow $\alpha_{22B}$ direction. Accordingly, it is possible to move the empty tray 200 from the tray remove region A5 to the device collect region A4.

The control portion 800 can control operations of each portion of the imaging portion 26 which will be described later in addition to the tray transport mechanism 11A, the tray transport mechanism 11B, the temperature adjustment portion 12, the device transport head 13, the device supply portion 14, the tray transport mechanism 15, the inspection portion 16, the device transport head 17, the device collect portion 18, the device transport head 20, the tray transport mechanism 21, the tray transport mechanism 22A, and the tray transport mechanism 22B.

The operator can set or confirm an operation condition or the like of the electronic component inspection apparatus 1 via the monitor 300. The monitor 300 includes a display screen 301 configured of, for example, a liquid crystal screen, and is disposed in an upper portion on the front side of the electronic component inspection apparatus 1. As illustrated in FIG. 1, on a right side in the drawing of the tray remove region A5, a mouse table 600 on which a mouse is mounted is provided. The mouse is used when operating the screen displayed on the monitor 300.

In addition, at a lower right part of FIG. 1 with respect to the monitor 300, the operation panel 700 is disposed. In addition to the monitor 300, the operation panel 700 is a panel for commanding a desirable operation to the electronic component inspection apparatus 1.

In addition, by combining radiant colors, the signal lamp 400 can notify the operator of an operation state or the like of the electronic component inspection apparatus 1. The signal lamp 400 is disposed in an upper portion of the electronic component inspection apparatus 1. In addition, in the electronic component inspection apparatus 1, a speaker 500 is embedded, and it is also possible to notify the operator of the operation state or the like of the electronic component inspection apparatus 1 by the speaker 500.

In the electronic component inspection apparatus 1, the tray supply region A1 and the device supply region A2 are partitioned by a first partition wall 231, the device supply region A2 and the inspection region A3 are partitioned by a second partition wall 232, the inspection region A3 and the device collect region A4 are partitioned by a third partition wall 233, and the device collect region A4 and the tray remove region A5 are partitioned by a fourth partition wall 234. In addition, the device supply region A2 and the device collect region A4 are partitioned by a fifth partition wall 235.

The most exterior of the electronic component inspection apparatus 1 is covered with a cover, and examples of the cover include a front cover 241, a side cover 242, a side cover 243, a rear cover 244, and a top cover 245.

As described above, in the device supply region A2, as the first mounting member on which the IC device 90 is mounted, the tray 200 that has been transported from the tray supply region A1 by the tray transport mechanism 11A, the temperature adjustment portion 12, and the device supply portion 14 are disposed.

However, in the first mounting member, there is a concern that the following phenomenon is generated. Here, the phenomenon in the device supply portion 14 will be described as a representative example among the tray 200, the temperature adjustment portion 12, and the device supply portion 14. In the device supply portion 14, originally, the IC device 90 is not mounted when the IC device 90 is supposed to be mounted, and on the contrary, the IC device 90 is mounted when the IC device 90 is not supposed to be mounted. As the reason of the former, for example, a case where the IC device 90 is dropped out while the device transport head 13 transports the IC device 90 from the temperature adjustment portion 12 to the device supply portion 14, is considered. As the reason of the latter, for example, a case where the device transport head 17 desired to grip the IC device 90 on the device supply portion 14 that has been moved to the inspection region A3, but the IC device 90 was not gripped and remained as it is, is considered. In addition, as another phenomenon, even when the IC device 90 is mounted, the mounting position is shifted from an appropriate position, or the IC device 90 is mounted in an inclined posture. As the reason thereof, for example, a case where, when the device transport head 13 mounts the IC device 90 onto the device supply portion 14, the device transport head 13 vibrates, and while maintaining the state, the gripped state of the IC device 90 is open, is considered.

In addition, while the phenomenon is generated, when the electronic component inspection apparatus 1 (electronic component transport apparatus 10) continues the operation, for example, the IC device 90 further stacks on the IC device 90 on the device supply portion 14, and there is a concern that a defect that the IC device 90 is damaged or the dropped-out IC device 90 is lost as it is, is generated.

Here, in the electronic component inspection apparatus 1 (electronic component transport apparatus 10) according to the invention, a configuration in which the defect can be solved is achieved. Hereinafter, the configuration and the action will be mainly described with reference to FIGS. 3 to 18.

Figure 4:
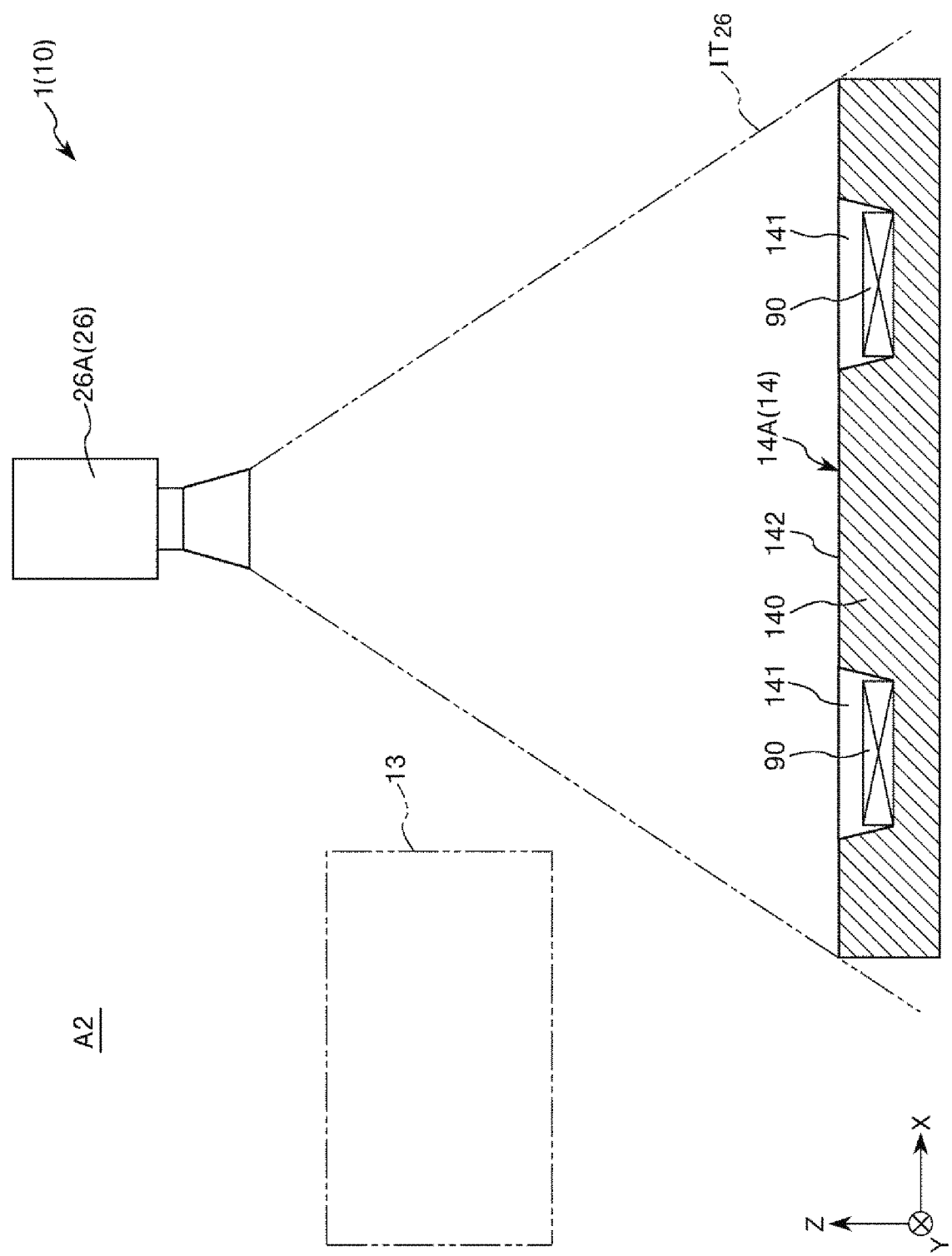
FIG. 4 is a view (sectional front view of a vertical part) when the imaging portion is viewed from an arrow direction A in FIG. 3.

As illustrated in FIG. 4, the device supply portion 14 (first mounting member) includes a plate member 140, and in the plate member 140, a plurality of mounting portions 141 (first mounting portion) in which the IC device 90 is accommodated and mounted, are provided. The mounting portion 141 is configured of a recess portion (pocket) which is open on an upper surface 142 of the plate member 140. In the embodiment, four mounting portions 141 are provided, and two of the four mounting portions 141 are provided in the X direction, and two of the four mounting portions 141 are provided in the Y direction (refer to FIGS. 5 to 14). Hereinafter, among the four mounting portions 141, the mounting portion 141 on a lower left side (coordinates (1, 1)) in FIGS. 5 to 14 is called "mounting portion 141a", the mounting portion 141 on the upper left side (coordinates (1, 2)) is called "mounting portion 141b", the mounting portion 141 on the lower right side (coordinates (2, 1)) is called "mounting portion 141c", and the mounting portion 141 on the upper right side (coordinates (2, 2)) is called "mounting portion 141d".

As described above, the device supply portion 14 can reciprocate between the device supply region A2 and the inspection region A3. In addition, in the device supply region A2, the device supply portion 14 stands by at a first standby position (position illustrated by a solid line in FIGS. 2 and 3), and the IC device 90 is transported by the device transport head 13. In addition, in the inspection region A3, the device supply portion 14 stands by at a second standby position (position illustrated by a broken line in FIG. 2), and the IC device 90 is transported by the device transport head 17.

As illustrated in FIGS. 3 and 4, the electronic component inspection apparatus 1 (electronic component transport apparatus 10) includes the imaging portion 26.

The imaging portion 26 is disposed above the first mounting member or the second mounting member in at least one region of the device supply region A2 and the device collect region A4. In other words, in the embodiment, one imaging portion 26 is disposed above the device supply portion 14A (first mounting member) which is positioned at the first standby position in the device supply region A2, and one imaging portion 26 is also disposed above the device supply portion 14B (first mounting member) positioned at the first standby position in the device supply region A2. Each of the imaging portions 26 is configured of various types of cameras, such as a charge coupled devices (CCD) camera or three-dimensional camera, and is fixed downward. Accordingly, the imaging portion 26 (hereinafter, referred to as "imaging portion 26A") on the device supply portion 14A can ensure an imaging region $IT_{26}$ as wide as possible, and can image the entire device supply portion 14A. In addition, similar to the imaging portion 26 (hereinafter, referred to as "imaging portion 26B") on the device supply portion 14B, it is possible to ensure the imaging region $IT_{26}$ as wide as possible, and to image the entire device supply portion 14B.

In addition, for example, the installation height in the device supply region A2 also matters, but in a case of a CCD camera of which the pixel is equal to or greater than 5000000, the imaging portion 26 can clearly (for example, clearly by a unit of 0.1 mm) image the device supply portion 14 of which the length in the X direction is equal to or greater than 240 mm.

As described above, the transport portion 25 includes the device transport head 13 (transport head) which is disposed in the device supply region A2 (one of the regions), and grips and transports the IC device 90 (electronic component). As illustrated in FIG. 4, even in a case of the highest height, the device transport head 13 (transport head) can move downward from the imaging portion 26. Accordingly, even when the device transport head 13 has moved, it is possible to prevent interference with the imaging portion 26.

In the device supply portion 14A and the device supply portion 14B, since the same phenomenon can be generated, and hereinafter, solving the defect in the device supply portion 14A will be described as a representative example.

In the electronic component inspection apparatus 1 (electronic component transport apparatus 10), it is possible to determine at least one of the presence or absence of the IC device 90 and the posture of the IC device 90 in the device supply portion 14A in the device supply region A2, and to notify the operator of the determination result. In addition, in the determination, a reference image and a captured image are used.

The reference image is an image set in advance, and is stored in the control portion 800. Examples of the reference image include images illustrated in FIGS. 5 to 9.

Figure 5:
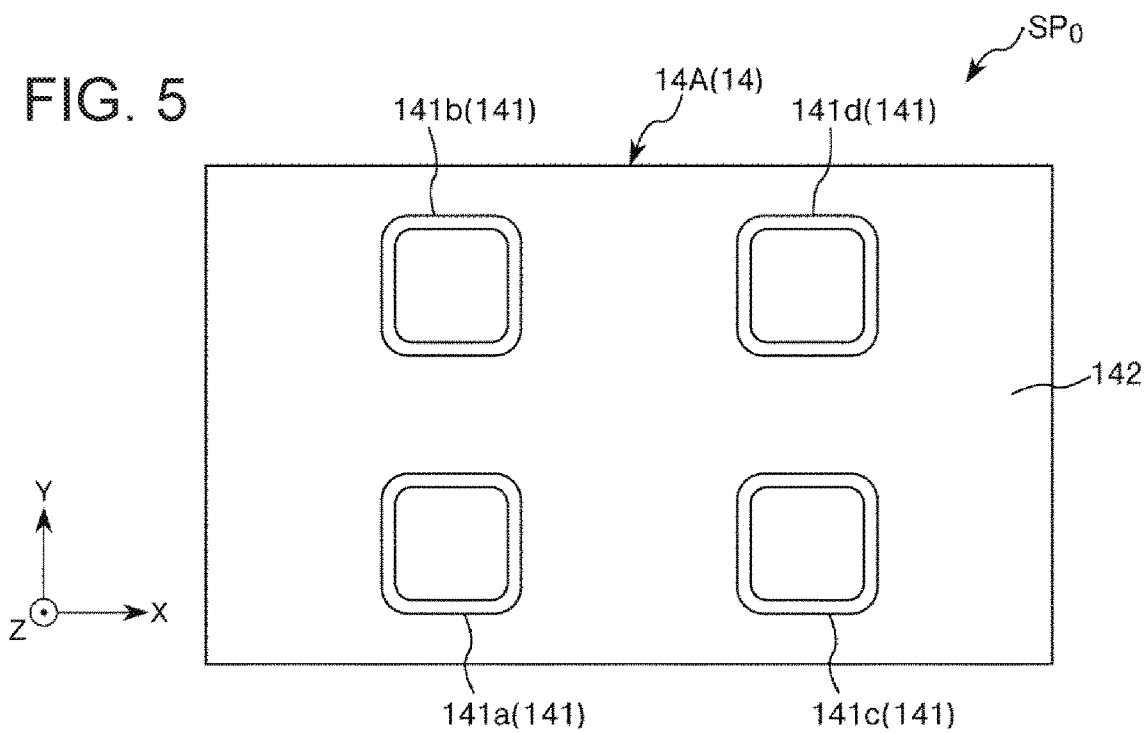
FIG. 5 is an example of a reference image stored in advance in the electronic component inspection apparatus illustrated in FIG. 1.

A reference image $SP_0$ illustrated in FIG. 5 is an image illustrating a state where the IC device 90 is not mounted on any of the mounting portion 141a, the mounting portion 141b, the mounting portion 141c, and the mounting portion 141d of the device supply portion 14A.

Figure 6:
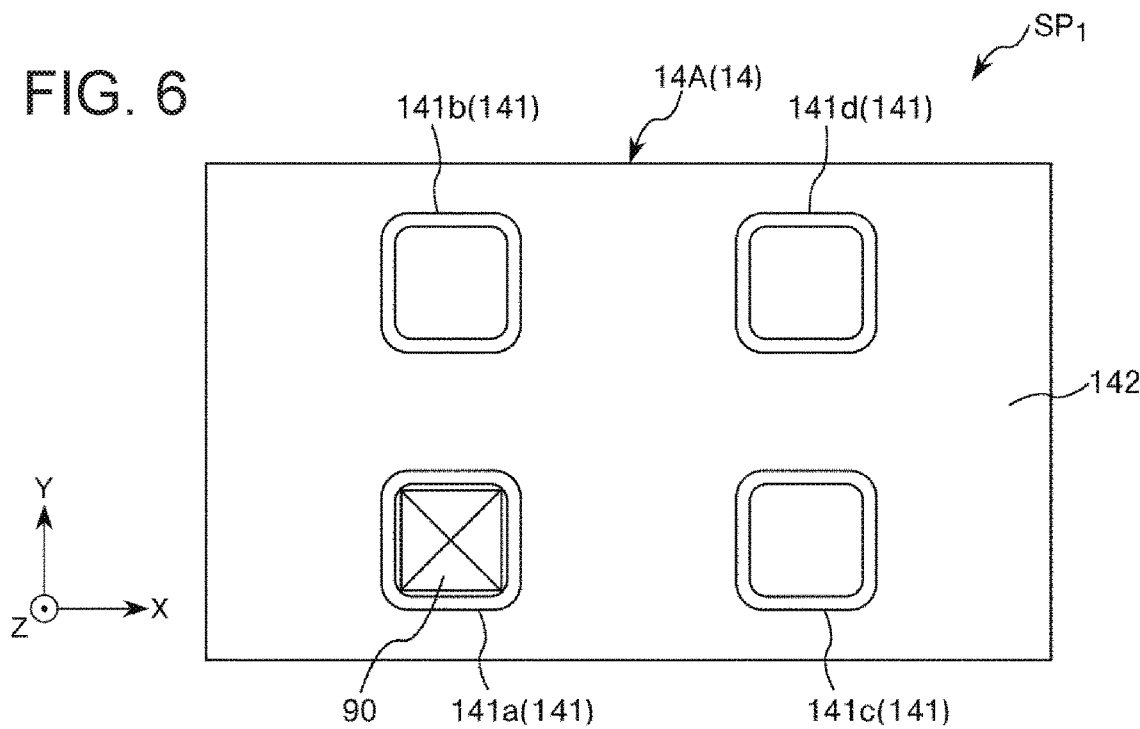
FIG. 6 is an example of the reference image stored in advance in the electronic component inspection apparatus illustrated in FIG. 1.

A reference image $SP_1$ illustrated in FIG. 6 is an image illustrating a state where the IC device 90 is mounted on the mounting portion 141a of the device supply portion 14A, and the IC device 90 is not mounted on the mounting portion 141b, the mounting portion 141c, and the mounting portion 141d.

A reference image $SP_2$ illustrated in FIG. 7 is an image illustrating a state where the IC devices 90 is mounted on each of the mounting portion 141a and the mounting portion 141b of the device supply portion 14A, and the IC device 90 is not mounted on the mounting portion 141c and the mounting portion 141d.

A reference image $SP_3$ illustrated in FIG. 8 is an image illustrating a state where the IC devices 90 is mounted on the mounting portion 141a, the mounting portion 141b, and the mounting portion 141c of the device supply portion 14A, and the IC device 90 is not mounted on the mounting portion 141d.

A reference image $SP_4$ illustrated in FIG. 9 is an image illustrating a state where the IC devices 90 is mounted on any of the mounting portion 141a, the mounting portion 141b, and the mounting portion 141c, and the mounting portion 141d of the device supply portion 14A.

The captured image is an image captured by the imaging portion 26. Examples of the captured image can include images illustrated in FIGS. 10 to 14.

A captured image $IP_1$ illustrated in FIG. 10 is an image illustrating a state where the IC device 90 is mounted on the mounting portion 141a of the device supply portion 14A, and the IC device 90 is not mounted on the mounting portion 141b, the mounting portion 141c, and the mounting portion 141d.

A captured image $IP_2$ illustrated in FIG. 11 is an image illustrating a state where the IC device 90 is mounted on the mounting portion 141a, the mounting portion 141b, and the mounting portion 141c of the device supply portion 14A, and the IC device 90 is not mounted on the mounting portion 141d.

A captured image $IP_3$ illustrated in FIG. 12 is an image illustrating a state where the IC device 90 is mounted on the mounting portion 141a, the mounting portion 141b, and the mounting portion 141c of the device supply portion 14A, the IC device 90 is mounted on the mounting portion 141d, but the IC device 90 is not mounted in an appropriate posture, that is, rotates around the Z-axis and is mounted at a shifted position.

Figure 13:
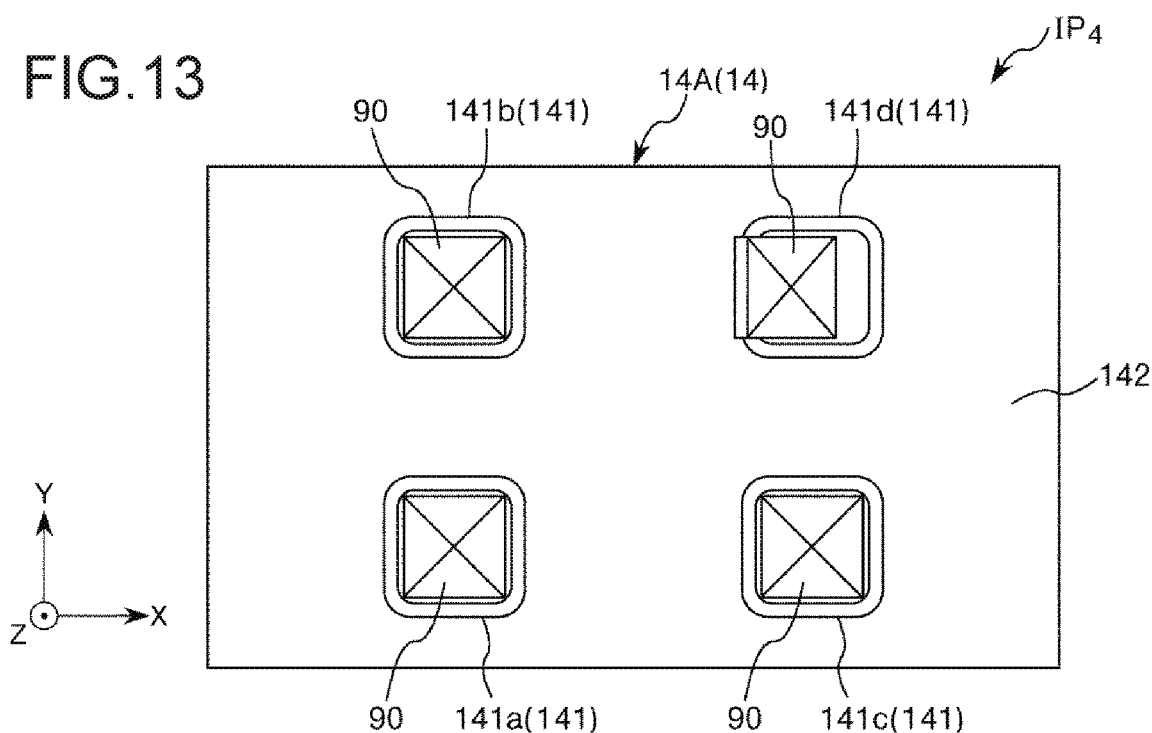
FIG. 13 is an example of the image (captured image) of a supply shuttle captured by the imaging portion illustrated in FIG. 3.

A captured image $IP_4$ illustrated in FIG. 13 is an image illustrating a state where the IC device 90 is mounted on the mounting portion 141a, the mounting portion 141b, and the mounting portion 141c of the device supply portion 14A, the IC device 90 is mounted on the mounting portion 141d, but the IC device 90 is not mounted in an appropriate (horizontal) posture, that is, is mounted in an inclined posture.

Figure 14:
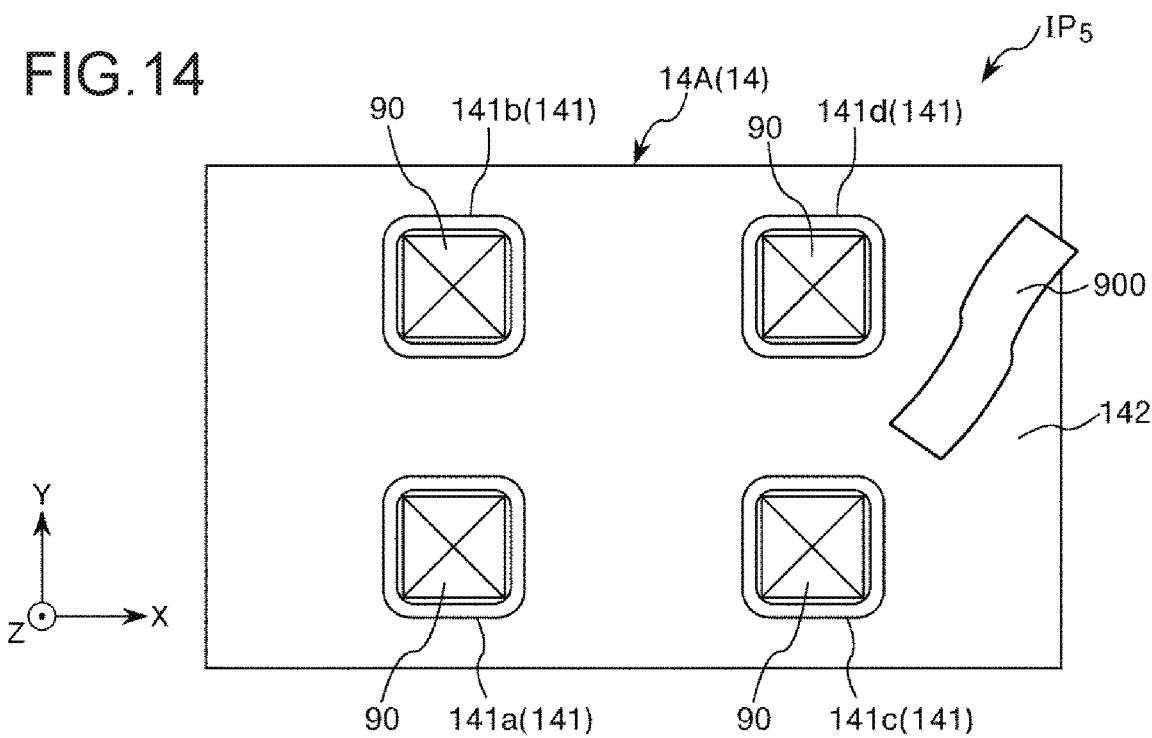
FIG. 14 is an example of the image (captured image) of a supply shuttle captured by the imaging portion illustrated in FIG. 3.

A captured image $IP_5$ illustrated in FIG. 14 is an image illustrating a state where the IC device 90 is mounted on any of the mounting portion 141a, the mounting portion 141b, the mounting portion 141c, and mounting portion 141d of the device supply portion 14A, but a foreign substance 900 other than the IC device 90 is mounted on the upper surface 142 of the device supply portion 14A. In addition, the foreign substance 900 is a label which sticks to a work specification or a handling instruction in FIG. 14, but in addition to this, for example, dust or waste may also be considered.

Figure 15:
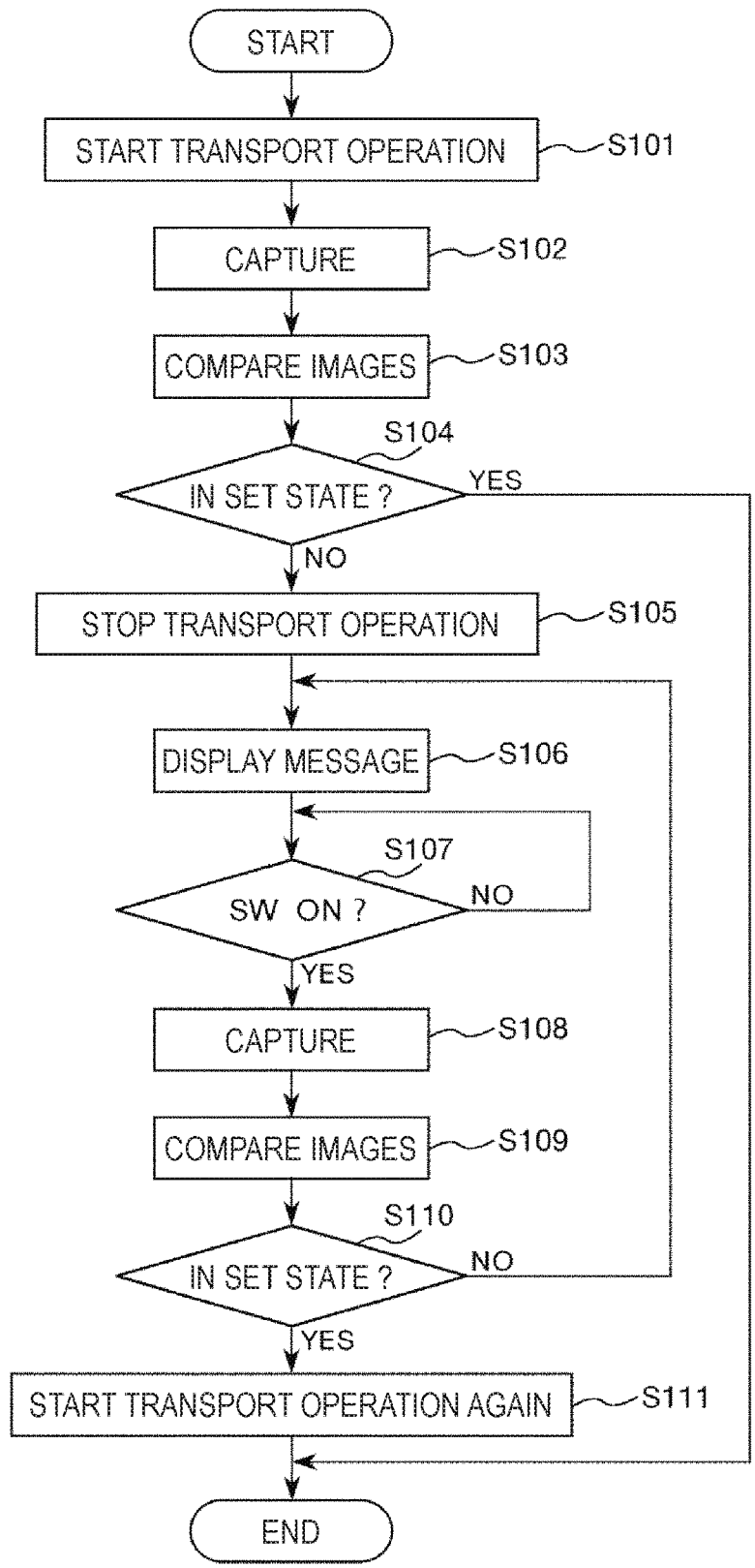
FIG. 15 is a flowchart illustrating a control program executed by the electronic component inspection apparatus illustrated in FIG. 1.

Next, by using the reference image and the captured image, a control program which determines at least one of the presence or absence of the IC device 90 and the posture of the IC device 90 in the device supply portion 14A, and notifies the operator of the determination result, will be described based on the flowchart illustrated in FIG. 15. Here, the control program will be described using a case where the reference image $SP_0$ is used as the reference image and the captured image $IP_1$ is obtained as the captured image, as an example (first example).

When the electronic component inspection apparatus 1 starts the transport operation of the IC device 90 from an initial state (stopped state) (step S101), by using the imaging portion 26, the device supply portion 14A which is positioned at the first standby position is imaged (step S102). Since the device supply portion 14A at this time starts from the initial state, the device supply portion 14A is supposed to be in a state where the IC device 90 is not mounted on any of the mounting portion 141a, the mounting portion 141b, the mounting portion 141c, and the mounting portion 141d. Therefore, as the captured image, an image which is the same as the reference image $SP_0$ is supposed to be obtained. However, the captured image $IP_1$ is obtained.

Next, by comparing the reference image $SP_0$ and the captured image $IP_1$ to each other (step S103), it is determined whether or not the device supply portion 14A is in a set state, that is, in a state where the IC device 90 is not mounted on any of the mounting portion 141a, the mounting portion 141b, the mounting portion 141c, and the mounting portion 141d (a state which is the same as that of the reference image $SP_0$) (step S104).

Figure 16:
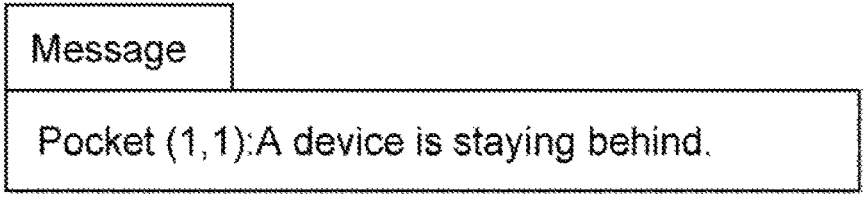
FIG. 16 is an example of a message displayed on a monitor of the electronic component inspection apparatus illustrated in FIG. 1.

When it is determined that the device supply portion 14A is not in the set state in step S104, the transport operation of the IC device 90 is stopped (step S105), and a message that says "the IC device 90 remains on the mounting portion 141a" as illustrated in FIG. 16 is displayed on the display screen 301 of the monitor 300 (step S106). The state is maintained until a start switch embedded in the operation panel 700 is turned ON in the next step S106. During this, for example, the operator can perform processing of removing the IC device 90 from the mounting portion 141a. In addition, in accordance with the message illustrated in FIG. 16, the notification which says the same contents may be performed by using the signal lamp 400 or the speaker 500.

Next, when it is determined that the start switch is turned ON in step S107, by the imaging portion 26, the device supply portion 14A which is positioned at the first standby position is imaged again (step S108). The device supply portion 14A at this time is supposed to be in a state where the IC device 90 is not mounted on any of the mounting portion 141a, mounting portion 141b, the mounting portion 141c, and the mounting portion 141d by the removing processing of the IC device 90 performed by the operator. Therefore, as the captured image, an image which is the same as the reference image $SP_0$ is supposed to be obtained, and practically, an image which is the same as the reference image $SP_0$ is obtained.

Next, similar to step S103, by comparing the images to each other (step S109), it is determined whether or not the device supply portion 14A is in a set state, that is, in a state where the IC device 90 is not mounted on any of the mounting portion 141a, the mounting portion 141b, the mounting portion 141c, and the mounting portion 141d (a state which is the same as that of the reference image $SP_0$) (step S110).

When it is determined that the device supply portion 14A is in the set state in step S110, the transport operation of the IC device 90 is started again (step S111). In addition, at this time, it is preferable to remove the message illustrated in FIG. 16 from the display screen 301. In addition, when it is determined that the device supply portion 14A is not in the set state in step S110, the process returns to step S106, and then, steps that follow the step S106 are executed in order.

In addition, as a second example, a case where the transport operation of the IC device 90 is continuously performed, and in the middle of this, the reference image $SP_4$ is used as the reference image and the captured image $IP_2$ is obtained as the captured image, will be described focusing on a point different from the first example.

In a case of the second example, the device supply portion 14A is supposed to be in a state where the IC device 90 is mounted on any of the mounting portion 141a, the mounting portion 141b, the mounting portion 141c, and the mounting portion 141d. Therefore, as the captured image, an image which is the same as the reference image $SP_4$ is supposed to be obtained. However, the captured image $IP_2$ is obtained.

Figure 17:
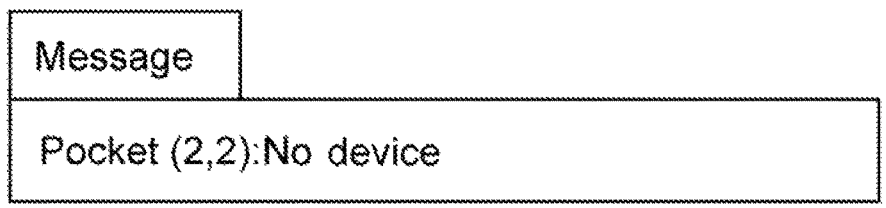
FIG. 17 is an example of a message displayed on the monitor of the electronic component inspection apparatus illustrated in FIG. 1.

In addition, by comparing the reference image $SP_4$ and the captured image $IP_2$ to each other, it is possible to determine that the IC device 90 is not mounted on the mounting portion 141d. In addition, at this time, a message that says "the IC device 90 is not mounted on the mounting portion 141d" as illustrated in FIG. 17 is displayed on the display screen 301 of the monitor 300. The operator who has confirmed the message can find the IC device 90 which should be mounted on the mounting portion 141d, for example, in the device supply region A2.

In addition, as a third example, a case where the transport operation of the IC device 90 is continuously performed, and in the middle of this, the reference image $SP_4$ is used as the reference image and the captured image $IP_3$ is obtained as the captured image, will be described focusing on a point different from the second example.

In a case of the third example, the device supply portion 14A is supposed to be in a state where the IC device 90 is mounted on any of the mounting portion 141a, the mounting portion 141b, the mounting portion 141c, and the mounting portion 141d. Therefore, as the captured image, an image which is the same as the reference image $SP_4$ is supposed to be obtained. However, the captured image $IP_3$ is obtained.

Figure 18:
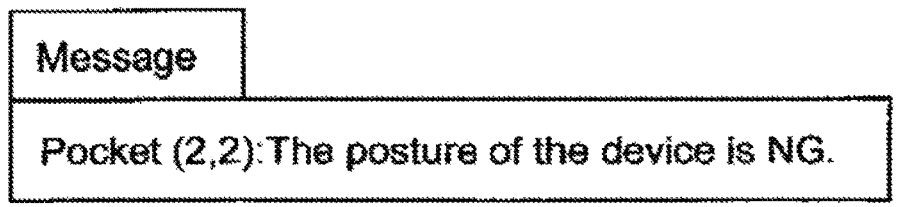
FIG. 18 is an example of a message displayed on the monitor of the electronic component inspection apparatus illustrated in FIG. 1.

In addition, by comparing the reference image $SP_4$ and the captured image $IP_3$ to each other, it is possible to determine that the IC device 90 mounted on the mounting portion 141d is not mounted in an appropriate posture, that is, rotates around the Z-axis and is at a shifted position. In addition, at this time, a message that says "the IC device 90 mounted on the mounting portion 141d is not in an appropriate posture" as illustrated in FIG. 18 is displayed on the display screen 301 of the monitor 300. The operator who has confirmed the message can correct the posture of the IC device 90 mounted on the mounting portion 141d to an appropriate posture.

In addition, as a fourth example, a case where the transport operation of the IC device 90 is continuously performed, and in the middle of this, the reference image $SP_4$ is used as the reference image and the captured image $IP_4$ is obtained as the captured image, will be described focusing on a point different from the third example.

In the fourth example, the device supply portion 14A is supposed to be in a state where the IC device 90 is mounted on any of the mounting portion 141a, the mounting portion 141b, the mounting portion 141c, and the mounting portion 141d. Therefore, as the captured image, an image which is the same as the reference image $SP_4$ is supposed to be obtained. However, the captured image $IP_4$ is obtained.

In addition, by comparing the reference image $SP_4$ and the captured image $IP_4$ to each other, it is possible to determine that the IC device 90 mounted on the mounting portion 141d is not mounted in an appropriate posture, that is, is mounted in an inclined state. In addition, at this time, a message that says "the IC device 90 mounted on the mounting portion 141d is not in an appropriate posture" as illustrated in FIG. 18 is displayed on the display screen 301 of the monitor 300. The operator who has confirmed the message can correct the posture of the IC device 90 mounted on the mounting portion 141d to an appropriate posture.

In addition, as a fifth example, a case where the transport operation of the IC device 90 is continuously performed, and in the middle of this, the reference image $SP_4$ is used as the reference image and the captured image $IP_5$ is obtained as the captured image, will be described focusing on a point different from the first example.

In a case of the fifth example, the device supply portion 14A is supposed to be in a state where the IC device 90 is mounted on any of the mounting portion 141a, the mounting portion 141b, the mounting portion 141c, and the mounting portion 141d. Therefore, as the captured image, an image which is the same as the reference image $SP_4$ is supposed to be obtained. However, the captured image $IP_5$ is obtained.

In addition, by comparing the reference image $SP_4$ and the captured image $IP_5$ to each other, it is possible to determine that the foreign substance 900 is mounted on the upper surface 142 of the device supply portion 14A. In addition, at this time, for example, a notification that says "the foreign substance 900 is mounted on the device supply portion 14A" can be performed by using the monitor 300, the signal lamp 400, and the speaker 500. The operator who has confirmed the notification can perform processing of removing the foreign substance 900 from the upper part of the device supply portion 14A.

In addition, in the first to fifth examples, the reference image $SP_0$ or the reference image $SP_4$ is used as the reference image, but in accordance with the transport operation of the IC device 90 of the electronic component inspection apparatus 1, it is also possible to appropriately use the reference image $SP_1$, the reference image $SP_2$, and the reference image $SP_3$.

As described above, the first mounting member is at least one of the device supply portion 14 (shuttle) which can reciprocate between the device supply region A2 (supply transport region) and the inspection region A3, the temperature adjustment portion 12 which can adjust the temperature of the IC device 90 (electronic component), and the tray 200 on which the IC device 90 (electronic component) before being transported in the device supply region A2 (supply transport region) is mounted, and the device supply portion 14 (device supply portion 14A) is representatively handled as one example in the embodiment. In addition, in the electronic component inspection apparatus 1 (electronic component transport apparatus 10), based on the imaging result obtained by imaging by the imaging portion 26, that is, by comparing the captured image $IP_1$ (imaging data) captured by the imaging portion 26 and the reference image $SP_0$ (reference data) set in advance to each other, it is possible to determine at least one of the presence or absence of the IC device 90 (electronic component) and the posture of the IC device 90 (electronic component) in the device supply portion 14A, and to notify the operator of the determination result. The operator who has confirmed the notification can visually recognize a state of the IC device 90 by device supply portion 14A, and to take a countermeasure which corresponds to the state. Accordingly, in the electronic component inspection apparatus 1 after the countermeasure, it is possible to prevent generation of a defect, such as a damage or loss of the IC device 90, and accordingly, the transport operation of the IC device 90 is stably and rapidly performed.

In addition, it is possible to specify that in which mounting portion 141 the state is among the four mounting portions 141. Accordingly, it is possible to take statistics (history) about by which mounting portion 141 the phenomenon is likely to be generated.

In addition, since the determination result is obtained based on the imaging result obtained by imaging by the imaging portion 26, even when the device supply portion 14A different from the mounting portion 141 on the second line and the second row, that is, the device supply portion 14A of which the number of dispositions or the disposition aspect of the mounting portion 141 is changed, is loaded, it is possible to omit the adjustment of various types of sensors (a presence/absence detection sensor of the IC device 90 or a posture detection sensor of the IC device 90) like the electronic component inspection apparatus (electronic component transport apparatus) of the related art. Accordingly, it is possible to rapidly correspond to various device supply portions 14A.

In addition, as described above, in the posture of the IC device 90, the inclination of the IC device 90 (electronic component) and the positional shift of the IC device 90 (electronic component) are included. The inclination and the positional shift are a posture which is relatively likely to be generated in an inappropriate posture, and the case where the inclination and the positional are included in the posture is preferable when the operator is notified of the determination result.

In addition, in the device supply region A2, a light radiation portion which radiates light with respect to the device supply portion 14A positioned at the first standby position may be provided. In a case where the IC device 90 is inclined on the device supply portion 14A, in the IC device 90, a part which the light from the light radiation portion illuminates and a part which becomes shadow are clearly expressed. Accordingly, it is possible to accurately determine that the IC device 90 is inclined.

In addition, as described above, in a case where the presence or absence of the IC device 90 (electronic component) is determined and in a case where the posture of the IC device 90 (electronic component) is determined, it is possible to perform different notification. In other words, in a case where the presence or absence of the IC device 90 is determined, the message illustrated in FIG. 16 or 17 can be displayed, and in a case where the posture of the IC device 90 is determined, the message illustrated in FIG. 18 can be displayed. Accordingly, the operator can grasp in which state the device supply portion 14A is in, and in accordance with the state, the operator can take an appropriate countermeasure.

Second Embodiment

Hereinafter, a second embodiment of the electronic component transport apparatus and the electronic component inspection apparatus according to the invention will be described with reference to FIGS. 19 and 20, but the description will focus on a point different from the above-described embodiment, and the description of the same contents will be omitted.

The embodiment is similar to the first embodiment except for the configuration of the device supply portion.

Figure 19:
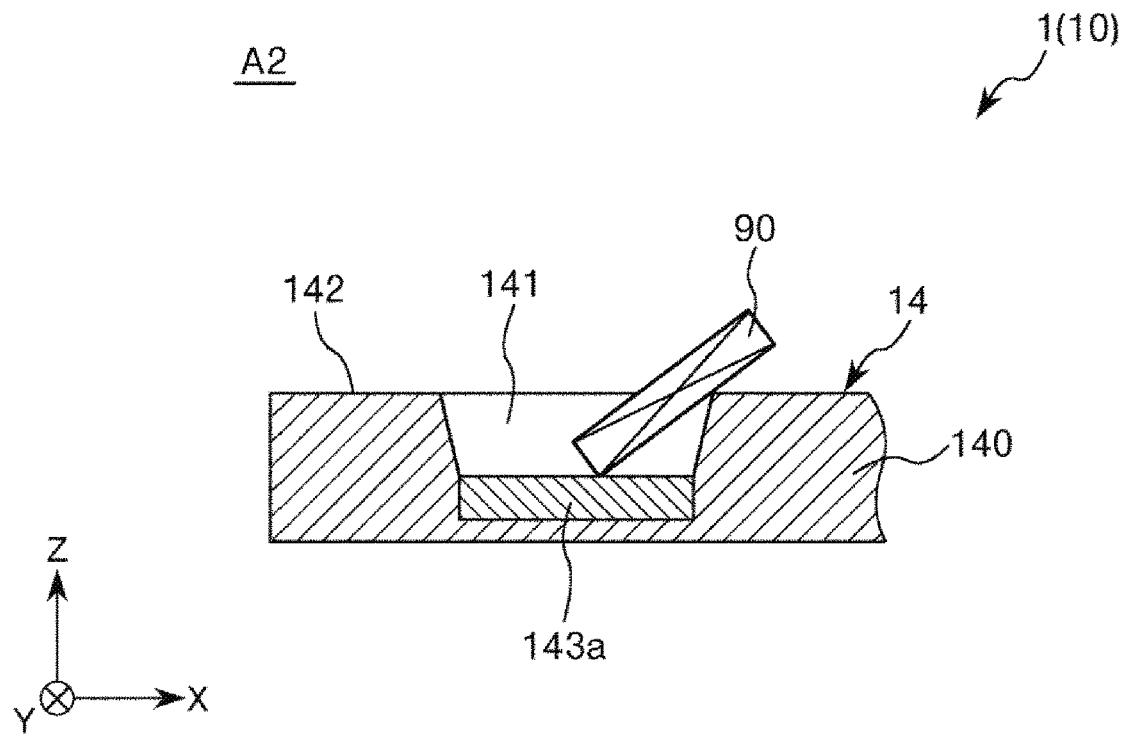
FIG. 19 is a vertical sectional view illustrating a supply shuttle of an electronic component inspection apparatus (second embodiment) according to the invention.
Figure 20:
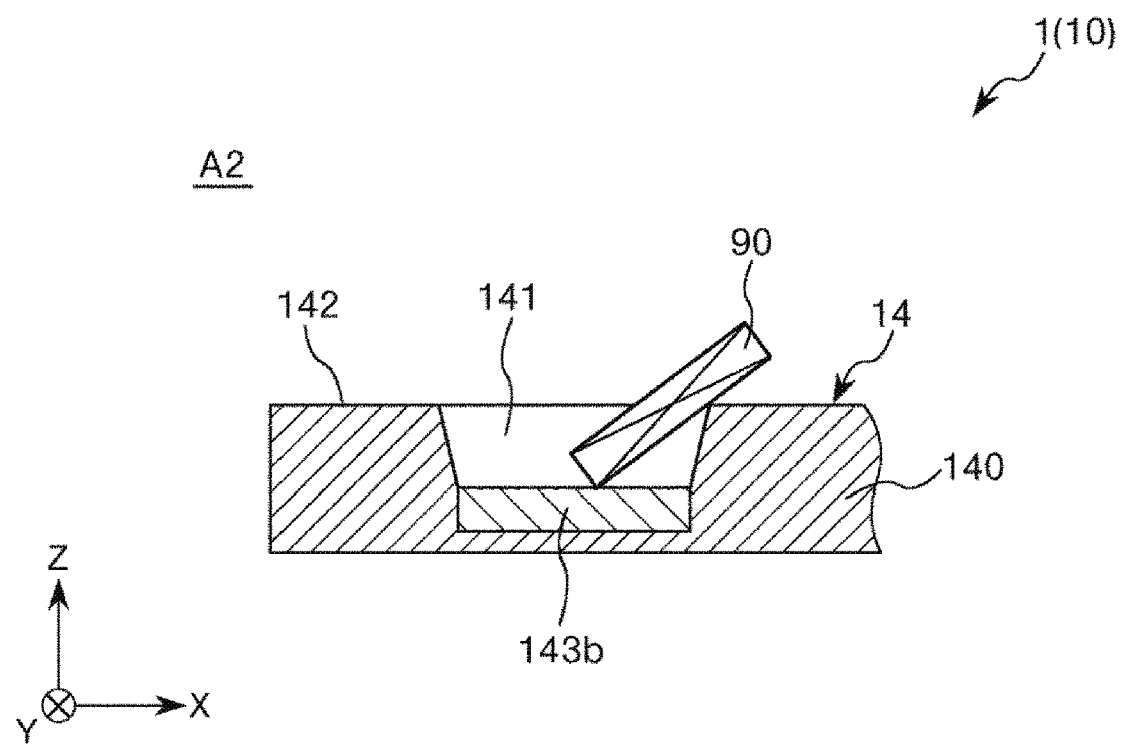
FIG. 20 is a vertical sectional view illustrating the supply shuttle of the electronic component inspection apparatus (second embodiment) according to the invention.

As illustrated in FIGS. 19 and 20, the mounting portion 141 (at least one mounting portion of the first mounting portion and the second mounting portion) of the device supply portion 14 is configured of the recess portion. In the embodiment, in the bottom portion of the mounting portion 141 (recess portion) before the IC device 90 (electronic component) is mounted, it is possible to exchange and install two types (plural types) of a reflector 143a and a reflector 143b which have a different degree of reflection of light. The reflector 143a in FIG. 19 can be a member obtained, for example, by performing electroless nickel plating with respect to a metal plate. The reflector 143b in FIG. 20 can be a member obtained, for example, by performing colored zinc plating with respect to a metal plate.

By the configuration, it is possible to change the contrast of the IC device 90 and the reflector 143a in the captured image in a case where the IC device 90 is mounted being inclined as illustrated in FIG. 19, and the contrast of the IC device 90 and the reflector 143b in the captured image in a case where the IC device 90 is mounted being inclined as illustrated in FIG. 20. Accordingly, by separately using the reflector 143a and the reflector 143b in accordance with the brightness in the device supply region A2, the inclined IC device 90 can be determined.

Third Embodiment

Figure 21:
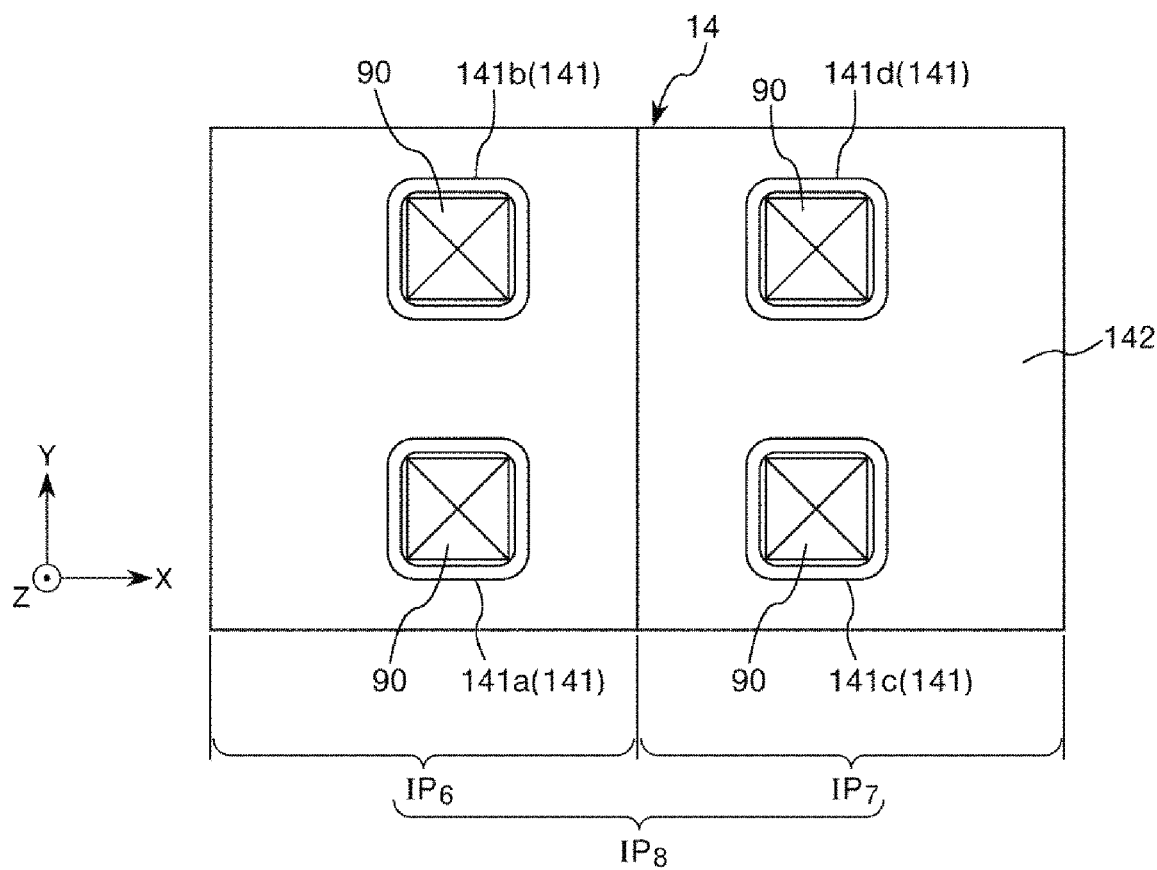
FIG. 21 is an example of an image (captured image) of a supply shuttle captured by an imaging portion of an electronic component inspection apparatus (third embodiment) according to the invention.

Hereinafter, a third embodiment of the electronic component transport apparatus and the electronic component inspection apparatus according to the invention will be described with reference to FIG. 21, but the description will focus on a point different from the above-described embodiments, and the description of the same contents will be omitted.

The embodiment is similar to the first embodiment except for the imaging aspect of the imaging portion.

The imaging portion 26 can divide and image the device supply portion 14 (the first mounting member or the second mounting member in one of the regions) in the device supply region A2. In this case, the imaging portion 26 is, for example, supported to be rotatable around the Y-axis, and in accordance with the rotation angle, it is possible to obtain a captured image $IP_6$ and a captured image $IP_7$ as illustrated in FIG. 21. In addition, by combining the captured image $IP_6$ and the captured image $IP_7$ to each other, it is possible to handle the image as one captured image $IP_{8w}$. For example, in a case where the imaging portion 26 is fixed as described in the first embodiment, according to the size of the device supply portion 14, there is a case where the entire device supply portion 14 is not captured, but in the embodiment, regardless of the size of the device supply portion 14, it is possible to obtain an image of the entire device supply portion 14. Accordingly, it is possible to determine the state in each of the mounting portions 141.

Fourth Embodiment

Hereinafter, a fourth embodiment of the electronic component transport apparatus and the electronic component inspection apparatus according to the invention will be described with reference to FIG. 22, but the description will focus on a point different from the above-described embodiments, and the description of the same contents will be omitted.

The embodiment is similar to the first embodiment except for the disposition location of the imaging portion.

Figure 22:
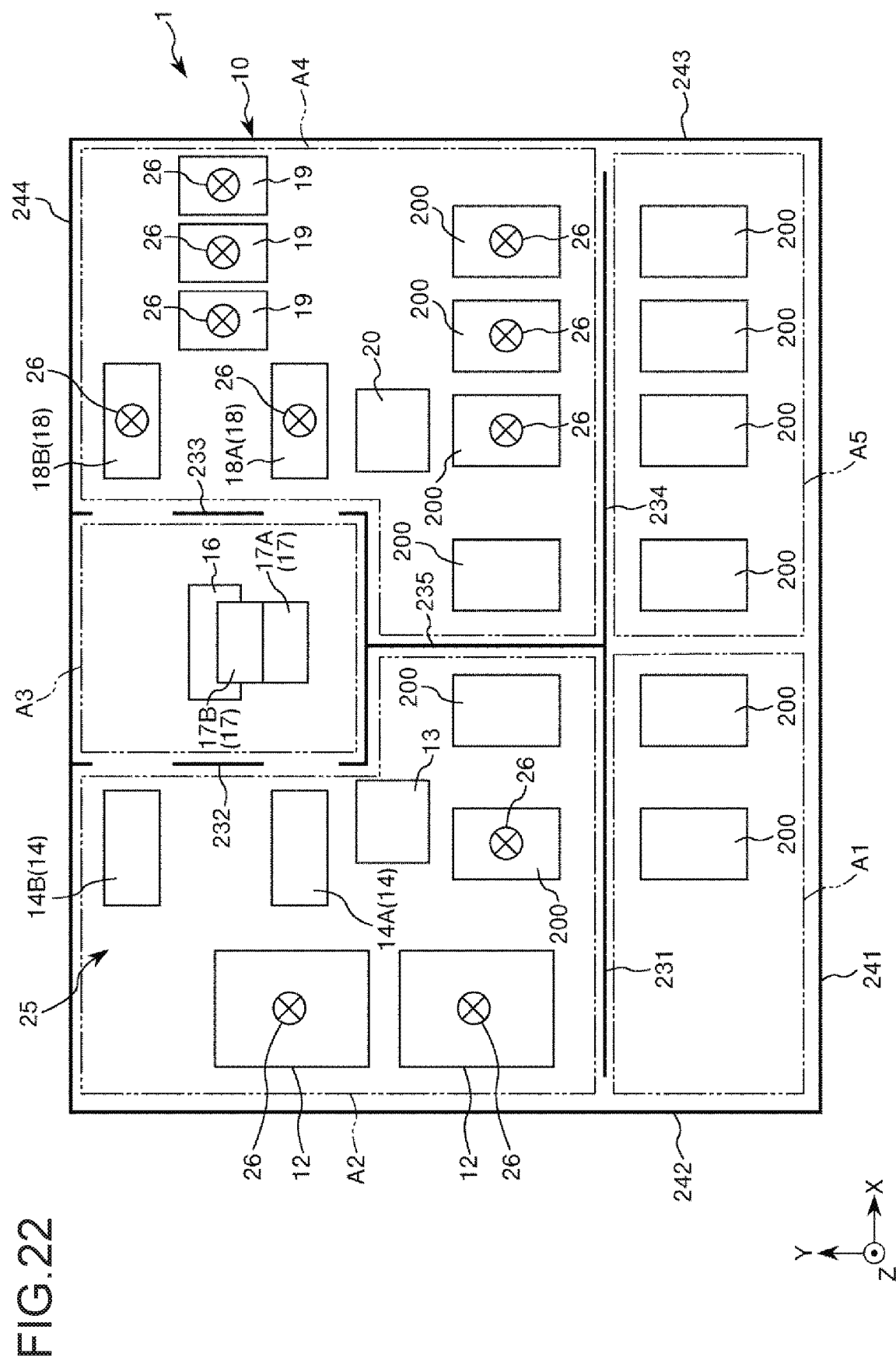
FIG. 22 is a plan view illustrating a disposition state of an imaging portion in an electronic component inspection apparatus (fourth embodiment) according to the invention.

As illustrated in FIG. 22, the electronic component transport apparatus 10 of the embodiment includes: the transport portion 25 which can transport the electronic component; the inspection region A3 in which the inspection portion 16 that inspects the electronic component can be disposed; the device supply region A2 (supply transport region) in which the first mounting member including the plurality of first mounting portions on which the electronic component is mounted can be disposed, and to which the electronic component before the inspection by the inspection portion 16 is transported; the device collect region A4 (collect transport region) in which the second mounting member including the plurality of second mounting portions on which the electronic component is mounted can be disposed, and to which the electronic component after the inspection by the inspection portion 16 is transported; and the imaging portion 26 which can image the first mounting member or the second mounting member, and it is possible to determine at least one of the presence or absence of the electronic component and the posture of the electronic component in the first mounting member or the second mounting member based on the imaging result obtained by imaging by the imaging portion 26, and to notify the operator of the determination result.

In the embodiment, the imaging portion 26 is disposed in both of the device supply region A2 and the device collect region A4.

In addition, the first mounting member is at least one of the device supply portion 14 (shuttle) which can reciprocate between the device supply region A2 (supply transport region) and the inspection region A3, the temperature adjustment portion 12 which can adjust the temperature of the IC device 90 (electronic component), and the tray 200 on which the IC device 90 (electronic component) before being transported in the device supply region A2 (supply transport region) is mounted, that is, which has been transported from the tray supply region A1, and corresponds to the temperature adjustment portion 12 and the tray 200 in the embodiment. In addition, in the device supply region A2, the imaging portions 26 are respectively disposed on the upper side (positive side in the Z direction) of the temperature adjustment portion 12 and the upper side (positive side in the Z direction) of the tray 200.

In addition, the second mounting member is at least one of the device collect portion 18 (shuttle) which can reciprocate between the inspection region A3 and the device collect region A4 (collect transport region), and the tray 200 on which the IC device 90 (electronic component) after being transported in the device collect region A4 (collect transport region), that is, which is transported to the tray remove region A5, corresponds to the device collect portion 18 and the tray 200 in the embodiment, and also further corresponds to the tray for collection 19. In addition, in the device collect region A4, the imaging portions 26 are respectively disposed on the upper side (positive side in the Z direction) of the device collect portion 18, on the upper side (positive side in the Z direction) of the tray 200, and on the upper side (positive side in the Z direction) of the tray for collection 19.

By the configuration, it is possible to determine the presence or absence of the IC device 90 or the posture of the IC device 90 in each of the first mounting members or in each of the second mounting members. In addition, it is possible to take a countermeasure (for example, removal of the IC device 90 or correction of the posture of the IC device 90) which corresponds to the state. Accordingly, it is possible to prevent generation of a defect that the IC device 90 is damaged or the like, and thus, the transport operation of the IC device 90 is stably and rapidly performed.

In addition, as illustrated in FIG. 22, the electronic component inspection apparatus 1 according to the invention includes the electronic component transport apparatus 10, and further includes the inspection portion 16 that inspects the electronic component. In other words, the electronic component inspection apparatus 1 according to the invention includes: the transport portion 25 which can transport the electronic component; the inspection portion 16 that inspects the electronic component; the inspection region A3 in which the inspection portion 16 can be disposed; the device supply region A2 (supply transport region) in which the first mounting member including the plurality of first mounting portions on which the electronic component is mounted can be disposed, and to which the electronic component before the inspection by the inspection portion 16 is transported; the device collect region A4 (collect transport region) in which the second mounting member including the plurality of second mounting portions on which the electronic component is mounted can be disposed, and to which the electronic component after the inspection by the inspection portion 16 is transported; and the imaging portion 26 which can image the first mounting member or the second mounting member, and it is possible to determine at least one of the presence or absence of the electronic component and the posture of the electronic component in the first mounting member or the second mounting member based on the imaging result obtained by imaging by the imaging portion 26, and to notify the operator of the determination result.

Accordingly, the electronic component inspection apparatus 1 having an advantage of the electronic component transport apparatus 10 of the above-described embodiments is obtained. In addition, it is possible to transport the electronic component to the inspection portion 16, and accordingly, to perform the inspection with respect to the electronic component by the inspection portion 16. In addition, it is possible to transport the electronic component after the inspection from the inspection portion 16.

In addition, in the embodiment, it is also possible to omit the arbitrary imaging portion 26 from the imaging portions 26.

In addition, as described in the second embodiment, even in the embodiment, at least one mounting portion of the first mounting portion and the second mounting portion is configured of the recess portion. In addition, in the bottom portion of the mounting portion (recess portion) before the IC device 90 (electronic component) is mounted, it is possible to exchange and install the plural types of reflectors having different degrees of reflection of the light. Accordingly, similar to the first embodiment, it is possible to determine the inclined IC device 90.

In addition, similar to the third embodiment, each of the imaging portions 26 in the device supply region A2 may be capable of dividing and imaging the corresponding first mounting member in the device supply region A2, and each of the imaging portions 26 in the device collect region A4 may be capable of dividing and imaging the corresponding second mounting member in the device collect region A4. Accordingly, it is possible to determine the state of the first mounting member or the second mounting member.

Above, the electronic component transport apparatus and the electronic component inspection apparatus according to the invention are described using the embodiments illustrated in the drawing, but the invention is not limited thereto, and each portion which configures the electronic component transport apparatus and the electronic component inspection apparatus can be replaced with an arbitrary configuration that can achieve similar functions. In addition, an arbitrary configuration member may be added.

In addition, the electronic component transport apparatus and the electronic component inspection apparatus according to the invention may combine two or more arbitrary configurations (characteristics) of each of the embodiments.

In addition, the imaging portion is fixed in the device supply region in the first embodiment, but the invention is not limited thereto, and may be supported to be movable in the device supply region. In this case, for example, it is possible to support the imaging portion by the device transport head that moves in the device supply region.

In addition, the imaging direction of the imaging portion is a perpendicularly downward direction in the first embodiment, but the invention is not limited thereto, and may be an obliquely downward direction. Accordingly, for example, on an outer side of the moving range of the device transport head that moves in the device supply region in a plan view, the imaging portion can be disposed.

In addition, processing of removing a part unnecessary for determining the presence or absence of the IC device or the posture of the IC device may be performed with respect to the image captured by the imaging portion.

In addition to the imaging by the imaging portion, a configuration in which the laser light is radiated toward the mounting member which is the imaging target and a change in shape of radiation in the mounting member is detected, may be added. Accordingly, it is possible to more accurately determine the state in the mounting member.

In addition, the number of dispositions of the first mounting portion is four in the first embodiment, but the invention is not limited thereto, and for example, the number may be two, three, five or more (similar in the second mounting portion). In addition, regarding the disposition aspect of the first mounting portion, for example, in a case where the number of dispositions of the first mounting portions is four, two of the first mounting portions are in the X direction and two of the first mounting portions are in the Y direction in the first embodiment, but it is needless to say that the invention is not limited thereto (similar in the second mounting portion).

In addition, in the second embodiment, there are two types of the reflectors, but the invention is not limited thereto, and the types may be three or more.

In addition, in the third embodiment, the mounting member which is the imaging target is divided into two and imaged, but the invention is not limited thereto, and for example, the mounting member which is the imaging target may be divided into three or more and imaged.

In addition, the invention is not limited to a case where one imaging portion is disposed with respect to one imaging target, and a plural number of imaging portions may be disposed. Accordingly, it is possible to divide the imaging target into plural imaging targets and image the imaging target.

The entire disclosure of Japanese Patent Application No. 2016-252558, filed Dec. 27, 2016 is expressly incorporated by reference herein.

What is claimed is:

1. An electronic component transport apparatus comprising:
   a transport portion that transports an electronic component;
   an inspection region in which an inspection portion that inspects the electronic component is disposed;
   a supply transport region in which a first mounting member including a plurality of first mounting portions on which the electronic component is mounted can be disposed, and to which the electronic component before the inspection by the inspection portion is transported;
   a collect transport region in which a second mounting member including a plurality of second mounting portions on which the electronic component is mounted can be disposed, and to which the electronic component after the inspection by the inspection portion is transported; and
   an imaging portion that images at least one of the first mounting member or the second mounting member,
   wherein at least one of the presence or absence of the electronic component and a posture of the electronic component in the first mounting member or the second mounting member is determined based on an imaging result obtained by imaging by the imaging portion, and an operator is notified of a determination result.

2. The electronic component transport apparatus according to claim 1,
   wherein the imaging portion is disposed in the supply transport region.

3. The electronic component transport apparatus according to claim 1,
   wherein the imaging portion is disposed in the collect transport region.

4. The electronic component transport apparatus according to claim 1,
   wherein the imaging portion is disposed in the supply transport region and in the collect transport region.

5. The electronic component transport apparatus according to claim 1,
   wherein at least one of the presence or absence of the electronic component and the posture of the electronic component is determined by comparing imaging data obtained by imaging by the imaging portion and reference data set in advance to each other, and an operator is notified of the determination result.

6. The electronic component transport apparatus according to claim 1,
wherein an inclination of the electronic component and a positional shift of the electronic component with respect to the first mounting member or the second mounting member, are included in the posture.

7. The electronic component transport apparatus according to claim 1,
wherein the imaging portion is disposed above the first mounting member or the second mounting member in one of the regions.

8. The electronic component transport apparatus according to claim 7,
wherein the transport portion includes a transport head which is disposed in one of the regions, and grips and transports the electronic component, and
wherein the transport head is movable downward from the imaging portion.

9. The electronic component transport apparatus according to claim 1,
wherein the first mounting member is at least one of a shuttle that reciprocates between the supply transport region and the inspection region, a temperature adjustment portion which adjusts the temperature of the electronic component, and a tray on which the electronic component before being transported in the supply transport region is mounted.

10. The electronic component transport apparatus according to claim 1,
wherein the second mounting member is at least one of a shuttle that reciprocates between the inspection region and the collect transport region, and a tray on which the electronic component after being transported in the collect transport region is mounted.

11. The electronic component transport apparatus according to claim 1,
wherein the imaging portion divides and images the first mounting member or the second mounting member in one of regions.

12. The electronic component transport apparatus according to claim 1,
wherein different notifications are performed in a case where the presence or absence of the electronic component is determined and in a case where the posture of the electronic component is determined.

13. The electronic component transport apparatus according to claim 1,
wherein at least one mounting portion of the first mounting portion and the second mounting portion is configured of a recess portion, and
wherein plural types of reflectors having different degrees of reflection of light are replaceable and installable in a bottom portion of the recess portion before the electronic component is mounted.

14. An electronic component inspection apparatus comprising:
a transport portion that transports an electronic component;
an inspection portion which inspects the electronic component;
an inspection region in which the inspection portion that inspects the electronic component is disposed;
a supply transport region in which a first mounting member including a plurality of first mounting portions on which the electronic component is mounted is disposed, and to which the electronic component before the inspection by the inspection portion is transported;
a collect transport region in which a second mounting member including a plurality of second mounting portions on which the electronic component is mounted is disposed, and to which the electronic component after the inspection by the inspection portion is transported; and
an imaging portion that images at least one of the first mounting member or the second mounting member,
wherein at least one of the presence or absence of the electronic component and a posture of the electronic component in the first mounting member or the second mounting member is determined based on an imaging result obtained by imaging by the imaging portion, and an operator is notified of a determination result.

* * * * *